(12) United States Patent
Panicucci et al.

(10) Patent No.: US 12,357,632 B2
(45) Date of Patent: Jul. 15, 2025

(54) METHODS OF TREATING CHOLANGIOCARCINOMA

(71) Applicant: QED Therapeutics, Inc., Palo Alto, CA (US)

(72) Inventors: Riccardo Panicucci, Bluffton, SC (US); Michael Monteith, Raleigh, NC (US); Gang Li, San Diego, CA (US); Susan Arangio, Los Altos, CA (US); Craig Berman, Mill Valley, CA (US); Michael Howland, San Francisco, CA (US); Daniel Mulreany, San Francisco, CA (US); Carl Dambkowski, San Mateo, CA (US)

(73) Assignee: QED Therapeutics, Inc., Palo Alto, CA (US)

( * ) Notice: Subject to any disclaimer, the term of this patent is extended or adjusted under 35 U.S.C. 154(b) by 640 days.

(21) Appl. No.: 17/613,651

(22) PCT Filed: May 28, 2020

(86) PCT No.: PCT/US2020/034881
§ 371 (c)(1),
(2) Date: Nov. 23, 2021

(87) PCT Pub. No.: WO2020/243273
PCT Pub. Date: Dec. 3, 2020

(65) Prior Publication Data
US 2022/0233536 A1 Jul. 28, 2022

Related U.S. Application Data

(60) Provisional application No. 62/853,431, filed on May 28, 2019.

(51) Int. Cl.
*A61K 31/50* (2006.01)
*A61K 31/506* (2006.01)
*A61P 35/04* (2006.01)

(52) U.S. Cl.
CPC ........... *A61K 31/506* (2013.01); *A61P 35/04* (2018.01)

(58) Field of Classification Search
CPC .................................................. A61K 31/506
See application file for complete search history.

(56) References Cited

U.S. PATENT DOCUMENTS

2015/0366866 A1  12/2015  Ali et al.

FOREIGN PATENT DOCUMENTS

WO  WO-2018/220206 A1  12/2018

OTHER PUBLICATIONS

Huynh et al. (2019) "Infigratinib Mediates Vascular Normalization, Impairs Metastatis, and Improves Chemotherapy in Hepatocellular Carcinoma," *Hepatology* 69(3):943-958.
International Search Report and Written Opinion for PCT/US2020/034881 dated Nov. 24, 2020, 15 pages.
Javle et al. (2018) "Phase II Study of BGJ398 in Patients With FGFR-Altered Advanced Cholangiocarcinoma," Journal of Clinical Oncology 36(3):276-282 (14 pages total with Authors' Disclosure).

*Primary Examiner* — Shawquia Jackson
(74) *Attorney, Agent, or Firm* — Goodwin Procter LLP

(57) ABSTRACT

Provided herein are methods of treating advanced or metastatic cholangiocarcinoma in a patient by administering to the patient infigratinib or a pharmaceutically acceptable salt thereof, wherein the patient has progression of the cholangiocarcinoma after previous administration of another therapy.

17 Claims, 4 Drawing Sheets

METHODS OF TREATING CHOLANGIOCARCINOMA

CROSS-REFERENCE TO RELATED APPLICATION

This application is a U.S. national stage patent application under 35 U.S.C. § 371 of International Application No. PCT/US2020/034881, filed on May 28, 2020, which claims the benefit of and priority to U.S. patent application No. 62/853,431, filed on May 28, 2019, the content of each of which is incorporated by reference herein in its entirety.

BACKGROUND

Cholangiocarcinoma, also known as biliary tract cancer, is a rare, heterogeneous malignancy which originates from the neoplastic transformation of cholangiocytes into intrahepatic, perihilar, or distal extrahepatic tumors (Alpini et al., 2001). In the United States, approximately 5,000-10,000 patients are diagnosed with cholangiocarcinoma of both the intra- and extrahepatic biliary system annually. Cholangiocarcinoma is more prevalent in Asia and Middle East, mostly because of a common parasitic infection of the bile duct (American Cancer Society, 2012). Men are slightly more likely to develop cholangiocarcinoma, while incidence increases with age in both sexes (Patel et al., 2002).

Typically, cholangiocarcinomas are adenocarcinomas and have poor prognosis with limited treatment alternatives. This is partly due to the late onset of symptoms and relative resistance to the therapies currently available. Moreover, conventional chemotherapy and radiation therapy (RT) have not been shown to be effective in prolonging long-term survival. Photodynamic therapy combined with stenting has been reported to be effective as a palliative treatment; however, it is not curative (Sirica, 2005). In April 2010, the ABC-02 trial was published, which was the first phase III randomized, controlled trial in this patient population where patients were randomly assigned to receive cisplatin plus gemcitabine or gemcitabine alone (Valle et al., 2010). In this study, the combination of gemcitabine/cisplatin demonstrated improved progression-free survival (PFS) and overall survival (OS) compared to gemcitabine alone. The median overall survival was 11.7 months in the cisplatin-gemcitabine group and 8.1 months in the gemcitabine group. The median progression-free survival was 8.0 months in the cisplatin-gemcitabine group and 5.0 months in the gemcitabine-only group. Still, cholangiocarcinoma patients relapsing after first line therapy have few therapeutic options, and there is no established second line standard of care. Response rates to currently available therapy are in the single digits (Lamarca et al., 2014).

The most recent guidelines regarding treatment of advanced biliary tract cancers, developed by the National Comprehensive Cancer Network (NCCN), recommend the use of gemcitabine, capecitabine, or 5-fluorouracil (5-FU), either as single agents or in combination with a platinum analog (oxaliplatin or cisplatin), or the combination of gemcitabine and capecitabine, with the combination of gemcitabine and cisplatin receiving a category 1 recommendation for first-line treatment of biliary tract cancer. None of these agents are FDA approved primarily for use in biliary tract cancers. Moreover, multi-agent chemotherapeutic approaches do not confer a durable benefit in patients with metastatic and/or relapsed disease, and fewer than 5% of patients survive 5 years after diagnosis of advanced disease.

Current NCCN guidelines for second-line treatment of biliary tract cancer (e.g., treatment for patients relapsing after receiving gemcitabine and/or cisplatin therapy) indicate that there is insufficient evidence to recommend specific regimens for second-line therapy in this group of patients.

Current European Society for Medical Oncology (ESMO) guidelines indicate that there is no established second-line systemic therapy following progression after first-line treatment although fluoropyrimidine-based therapy (either in monotherapy or in combination with other cytotoxics) is sometimes used.

Thus, there is a real need to develop novel therapeutic strategies for cholangiocarcinoma based on exploiting select molecular targets that would significantly impact clinical outcomes.

SUMMARY

In one aspect, provided herein are methods of treating advanced or metastatic cholangiocarcinoma in a patient in need thereof, the method comprising administering an effective amount of infigratinib, or a pharmaceutically acceptable salt thereof, wherein the patient has progression of the cholangiocarcinoma after previous administration of another therapy.

In certain embodiments, the previous administration of another therapy is a therapy for advanced or metastatic cholangiocarcinoma. In some embodiments, the previous administration of another therapy is an administration of a chemotherapeutic agent. In some embodiments, the previous administration of a chemotherapeutic agent is a gemcitabine-containing regimen.

In certain embodiments, the cholangiocarcinoma has a FGFR1 gene fusion, translocation or another genetic alteration. In certain embodiments, the cholangiocarcinoma has a FGFR2 gene fusion, translocation or another genetic alteration. In some embodiments, the FGFR2 gene fusion comprises a FGFR2 gene fusion partner selected from the group consisting of 10Q26.13, AFF1, AFF4, AHCYL1, ALDH1L2, ARFIP1, BICC1, C10orf118, C7, CCDC147, $CCDCl_6$, CELF2, CREB5, CREM, DNAJC12, HOOK1, KCTD1, KIAA1217, KIAA1598, KIFC3, MGEA5, NOL4, NRAP, OPTN, PARK2, PAWR, PCMI, PHLDB2, PPHLN1, RASAL2, SFMBT2, SLMAP, SLMAP2, SORBS1, STK26, STK3, TACC3, TBC1D1, TFEC, TRA2B, UBQLN1, VCL, WAC, and ZMYM4. In certain embodiments, the cholangiocarcinoma has a FGFR3 gene fusion, translocation or another genetic alteration.

In certain embodiments, administering an effective amount of infigratinib, or a pharmaceutically acceptable salt thereof, comprises administering orally about 125 mg of infigratinib, or a pharmaceutically acceptable salt thereof, once daily.

In certain embodiments, administering an effective amount of infigratinib, or a pharmaceutically acceptable salt thereof comprises a 28-day cycle, wherein about 125 mg of infigratinib, or a pharmaceutically acceptable salt thereof, is administered once daily to the patient for 3 consecutive weeks (21 days), and no infigratinib is administered for 1 week (7 consecutive days).

In certain embodiments, the about 125 mg of infigratinib or a pharmaceutically acceptable salt thereof is provided as a 100 mg unit dose and a 25 mg unit dose. In certain embodiments, the about 125 mg of infigratinib or a pharmaceutically acceptable salt thereof is provided as a unit dose.

In certain embodiments, the advanced or metastatic cholangiocarcinoma is histologically or cytologically confirmed.

In certain embodiments, the cholangiocarcinoma has a FGFR1, FGFR2 and/or FGFR3 mutation. In some embodiments, the FGFR1, FGFR 2 and/or FGFR3 mutation is selected from the group consisting of FGFR1 G818R, FGFR1 K656E, FGFR1 N546K, FGFR1 R445W, FGFR1 T141R, FGFR2 A315T, FGFR2 C382R, FGFR2 D336N, FGFR2 D471N, FGFR2 E565A, FGFR2 I547V, FGFR2 K641R, FGFR2 K659E, FGFR2 K659M, FGFR2 L617V, FGFR2 N549H, FGFR2 N549K, FGFR2 N549S, FGFR2 N549Y, FGFR2 N550K, FGFR2 P253R, FGFR2 S252W, FGFR2 V395D, FGFR2 V564F, FGFR2 Y375C, FGFR3 A391E, FGFR3 D785Y, FGFR3 E627K, FGFR3 G370C, FGFR3 G380R, FGFR3 K650E, FGFR3 K650M, FGFR3 K650N, FGFR3 K650T, FGFR3 K652E, FGFR3 N540S, FGFR3 R248C, FGFR3 R399C, FGFR3 S131L, FGFR3 S249C, FGFR3 S371C, FGFR3 V555M, FGFR3 V677I, FGFR3 Y373C, FGFR4 D425N, FGFR4 R183S, FGFR4 R394Q, FGFR4 R610H, FGFR4 V510L, and combinations thereof.

In certain embodiments, the cholangiocarcinoma has a FGFR2 gene fusion and a FGFR2 mutation.

In certain embodiments, the cholangiocarcinoma has amplification of FGFR1, FGFR2 and/or FGFR3.

In certain embodiments, the previous administration of another therapy is administration of a receptor tyrosine kinase inhibitor. In certain embodiments, the receptor tyrosine kinase inhibitor is a selective non-covalently binding inhibitor of FGFR1, FGFR2 and/or FGFR3. In some embodiments, the selective non-covalently binding inhibitor of FGFR1, FGFR2 and/or FGFR3 is selected from the group consisting of pemigatinib, rogaratinib, derazantinib, Debio1347, AZD4547 and combinations thereof. In certain embodiments, the receptor tyrosine kinase inhibitor is a selective non-covalently binding inhibitor of FGFR1, FGFR2, FGFR3 and/or FGFR4. In some embodiments, the selective non-covalently binding inhibitor of FGFR1, FGFR2, FGFR3 and/or FGFR4 is selected from the group consisting of erdafitinib, LY2874455, PRN 1371, ASP5878, and combinations thereof. In certain embodiments, the receptor tyrosine kinase inhibitor is a selective covalently binding inhibitor of FGFR1, FGFR2, FGFR3 and/or FGFR4. In some embodiments, the selective covalently binding inhibitor of FGFR1, FGFR2, FGFR3 and/or FGFR4 is TAS120. In certain embodiments, the receptor tyrosine kinase inhibitor is a non-selective tyrosine kinase inhibitor. In some embodiments, the non-selective tyrosine kinase inhibitor is selected from the group consisting of ponatinib, dovitinib, levatanib, ACTB-1003, Ki8751, lucitinib, masitinib, mubritinib, nintedanib, orantinib, PD089828, and combinations thereof.

In certain embodiments, the previous administration of another therapy is administration of another selective FGFR inhibitor. In some embodiments, the another selective FGFR inhibitor is selected from the group consisting of pemigatinib, rogaratinib, derazantinib, AZD4547, Debio1347, ASP5878, erdafitinib, LY2874455, PRN1371, TAS120, and combinations thereof. In certain embodiments, the another selective FGFR inhibitor is a selective covalently binding FGFR inhibitor. In some embodiments, the selective covalently binding FGFR inhibitor is TAS120. In certain embodiments, the another selective FGFR inhibitor is a selective non-covalently binding FGFR inhibitor. In some embodiments, the selective non-covalently binding FGFR inhibitor is pemigatinib, rogaratinib, derazantinib, AZD4547 and combinations thereof.

DETAILED DESCRIPTION

Figure 1:
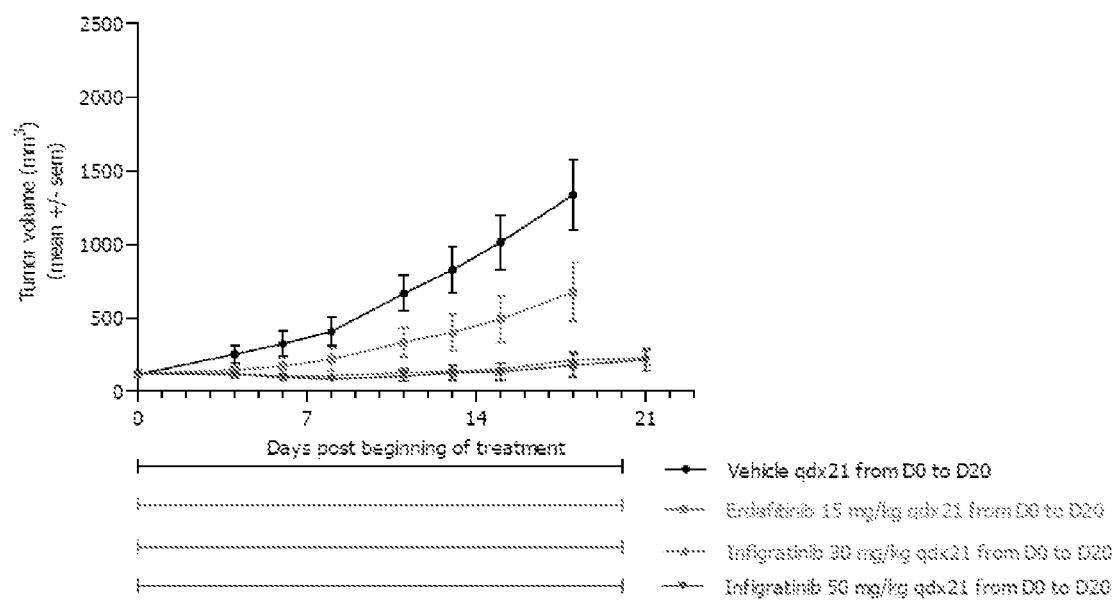
FIG. 1 is an overlay of tumor growth curves (mean tumor volume over time) for (i) vehicle qdx21, (ii) erdafitinib 15 mg/kg qdx21, (iii) infigratinib 30 mg/kg qdx21, and (iv) infigratinib 50 mg/kg qdx21, in human Vex-MR086M1 ureter carcinoma xenograft model (XTS-2034), as further described in Example 5.

As generally described herein, the present disclosure provides methods of treating advanced or metastatic cholangiocarcinoma in a patient in need thereof, for example, when the patient has progression of the cholangiocarcinoma after previous administration of another therapy.

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified. Further, if a variable is not accompanied by a definition, then the previous definition of the variable controls.

As used herein, "pharmaceutical composition" or "pharmaceutical formulation" refers to the combination of an active agent with a carrier, inert or active, making the composition especially suitable for diagnostic or therapeutic use in vivo or ex vivo.

"Pharmaceutically acceptable" means approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable salt" refers to any salt of an acidic or a basic group that may be present in a compound of the present invention (e.g., infigratinib), which salt is compatible with pharmaceutical administration.

As is known to those of skill in the art, "salts" of compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is C1-4 alkyl, and the like.

Examples of salts include, but are not limited, to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $K^+$, $Ca^{2+}$, $NH_4^+$, and $NW_4^+$ (where W can be a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "pharmaceutically acceptable excipient" refers to a substance that aids the administration of an active agent to and/or absorption by a subject and can be included in the compositions of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, PA (1975).

The term "AUC" refers to the area under the time/plasma concentration curve after administration of the pharmaceutical composition. $AUC_{0\text{-}infinity}$ denotes the area under the plasma concentration versus time curve from time 0 to infinity; $AUC_{0\text{-}t}$ denotes the area under the plasma concentration versus time curve from time 0 to time t. It should be appreciated that AUC values can be determined by known methods in the art.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

The term "$C_{max}$" refers to the maximum concentration of a therapeutic agent (e.g., infigratinib) in the blood (e.g., plasma) following administration of the pharmaceutical composition.

The term "$t_{max}$" refers to the time in hours when $C_{max}$ is achieved following administration of the pharmaceutical composition comprising a therapeutic agent (e.g., infigratinib).

As used herein, "solid dosage form" means a pharmaceutical dose(s) in solid form, e.g., tablets, capsules, granules, powders, sachets, reconstitutable powders, dry powder inhalers and chewables.

As used herein, "administering" means oral administration, administration as a suppository, topical contact, intravenous administration, parenteral administration, intraperitoneal administration, intramuscular administration, intralesional administration, intrathecal administration, intracranial administration, intranasal administration or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). Infigratinib, or a pharmaceutically acceptable salt thereof, can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

The terms "disease," "disorder," and "condition" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (e.g., "therapeutic treatment").

In general, an "effective amount" of a compound refers to an amount sufficient to elicit the desired biological response, e.g., to treat cholangiocarcinoma. As will be appreciated by those of ordinary skill in this art, the effective amount of a compound of the disclosure may vary depending on such factors as the desired biological endpoint, the pharmacokinetics of the compound, the disease being treated, the mode of administration, and the age, weight, health, and condition of the subject.

Infigratinib

Infigratinib, as depicted in formula (I), is a selective and ATP-competitive pan-fibroblast growth factor receptor (FGFR) kinase inhibitor, also known as 3-(2,6-dichloro-3,5-dimethoxyphenyl)-1-{6-[4-(4-ethyl-1-piperazin-1-yl)phenylamino]-pyrimidinyl-4-yl}-1-methylurea. Infigratinib selectively inhibits the kinase activity of FGFR1, FGFR2, and FGFR3.

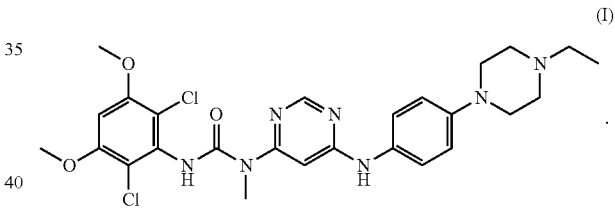

(I)

A method of chemically synthesizing infigratinib (including Example 1 provided herein), several crystalline and amorphous forms of infigratinib (including the anhydrous crystalline monophosphate salt described herein) and methods of preparing said forms (including Example 2 provided herein) were described in U.S. Pat. No. 9,067,896, which is incorporated by reference in its entirety herein.

In one aspect, provided herein is infigratinib, or a pharmaceutically acceptable salt thereof, for the treatment of advanced or metastatic cholangiocarcinoma in a patient in need thereof.

In certain embodiments, provided herein is a pharmaceutically acceptable salt of infigratinib for the treatment of advanced or metastatic cholangiocarcinoma in a patient in need thereof. In some embodiments, the pharmaceutically acceptable salt of infigratinib is a monophosphate salt. The monophosphate salt of infigratinib may also be referred to as BGJ398.

In some embodiments, the monophosphate salt of infigratinib is an anhydrous crystalline monophosphate salt. In some embodiments, the anhydrous crystalline monophosphate salt has an X-ray powder diffraction (XRPD) pattern comprising a characteristic peak, in terms of 2θ, at about 15.0° or 15.0°±0.2°. In some embodiments, the X-ray powder diffraction pattern of the anhydrous crystalline monophosphate salt further comprises one or more characteristic peaks, in terms of 2θ, selected from peaks at about 13.7°±0.2°, about 16.8°±0.2°, about 21.3°±0.2° and about 22.4°±0.2°. In some embodiments, the X-ray powder diffraction pattern of the anhydrous crystalline monophosphate salt further comprises one or more characteristic peaks, in terms of 2θ, selected from peaks at about 9.2°, about 9.6°, about 18.7°, about 20.0°, about 22.9°, and about 27.2°. In some embodiment, the anhydrous crystalline monophosphate salt has an XRPD pattern comprising at least three characteristic peaks, in terms of 2θ, selected from the peaks at about 13.7°, about 15°, about 16.8, about 21.3° and about 22.4°. In some embodiments, the X-ray powder diffraction pattern for the anhydrous crystalline monophosphate salt may comprise one, two, three, four, five, six, seven, eight, nine, ten or eleven characteristic peaks, in terms of 2θ, selected from the peaks at about 9.2°, about 9.6°, about 13.7°, about 15°, about 16.8°, about 18.7°, about 20.0°, about 21.3° and about 22.4°, about 22.9°, and about 27.2.

Pharmaceutical Compositions

Pharmaceutical compositions of infigratinib and methods of preparing said pharmaceutical compositions (e.g., including Example 3 described herein) were described in U.S. Patent Application Publication No. 2017/0007602, which is incorporated by reference in its entirety herein.

In one aspect, provided herein is a pharmaceutical composition comprising infigratinib, or a pharmaceutically acceptable salt thereof, and a pharmaceutically acceptable excipient, for the treatment of advanced or metastatic cholangiocarcinoma in a patient in need thereof.

In certain embodiments, a pharmaceutical composition of the present teachings comprises:
  (a) from about 20% to about 60% infigratinib, or a pharmaceutically acceptable salt thereof, by weight in its free base form;
  (b) from about 0.5% to about 5% by weight of hydroxypropylmethylcellulose;
  (c) from about 1% to about 4% by weight of crosslinked polyvinylpyrrolidone; and
  (d) a filler selected from the group consisting of a cellulose, lactose, mannitol, and combinations thereof,
  wherein the weight percentages are based on the total weight of the pharmaceutical composition.

In certain embodiments, the pharmaceutical composition comprises from about 30% to about 45% of infigratinib, or a pharmaceutically acceptable salt thereof, by weight in its free base form.

In certain embodiments, the pharmaceutical composition comprises from about 2% to about 4% of hydroxypropylmethylcellulose. In certain embodiments, the pharmaceutical composition comprises from about 2% to about 4% of crosslinked polyvinylpyrrolidone.

In certain embodiments, the pharmaceutical composition further comprises:
  (e) from about 10% to about 95% of one or more fillers, by weight based on the total weight of the pharmaceutical composition;
  (f) from about 0.1% to about 3% of one or more lubricants, by weight based on the total weight of the pharmaceutical composition; and
  (g) from about 0.10% to about 2% of one or more glidants, by weight based on the total weight of the pharmaceutical composition.

In certain embodiments, the one or more fillers is selected from the group consisting of microcrystalline cellulose, lactose, and/or mannitol.

In certain embodiments, the one or more lubricants in the pharmaceutical composition is present in an amount of from about 0.2% to about 2%, by weight based on the total weight of the pharmaceutical composition. In some embodiments, the one or more lubricants is magnesium stearate.

In certain embodiments, the one or more glidants is present in the pharmaceutical formulation in an amount of from about 0.10% to about 0.5%, by weight based on the total weight of the pharmaceutical composition. In some embodiments, the one or more glidants is colloidal silicon dioxide (colloidal silica).

In certain embodiments, the amount of infigratinib, or a pharmaceutically acceptable salt thereof, in the pharmaceutical composition is from about 25 mg to about 150 mg, about 50 mg to about 150 mg, about 75 mg to about 150 mg, about 100 mg to about 150 mg, about 125 mg to about 150 mg, about 25 mg to about 125 mg, about 25 mg to about 100 mg, about 25 mg to about 75 mg, about 25 mg to about 50 mg, about 50 mg to about 125 mg, about 50 mg to about 100 mg, about 50 mg to about 75 mg, about 75 mg to about 125 mg, about 75 mg to about 100 mg, or about 100 mg to about 125 mg. In some embodiments, the amount of infigratinib, or a pharmaceutically acceptable salt thereof, in the pharmaceutical composition is from about 100 mg to about 150 mg of infigratinib or a pharmaceutically acceptable salt thereof.

In certain embodiments, the amount of infigratinib, or a pharmaceutically acceptable salt thereof, in the pharmaceutical composition is about 25 mg, about 50 mg, about 75 mg, about 100 mg, about 125 mg, about 150 mg, about 175 mg, or about 200 mg. In some embodiments, the amount of infigratinib, or a pharmaceutically acceptable salt thereof, in the pharmaceutical composition is about 125 mg. In some embodiments, the amount of infigratinib, or a pharmaceutically acceptable salt thereof, in the pharmaceutical composition is about 100 mg. In some embodiments, the amount of infigratinib, or a pharmaceutically acceptable salt thereof, in the pharmaceutical composition is about 25 mg.

In another aspect, provided herein is a pharmaceutical composition comprising about 125 mg infigratinib, or a pharmaceutically acceptable salt thereof, and a pharmaceutically acceptable excipient, for the treatment of advanced or metastatic cholangiocarcinoma in a patient in need thereof.

In certain embodiments, the pharmaceutical compositions comprise an effective amount of a pharmaceutically acceptable salt of infigratinib. In some embodiments, the pharmaceutically acceptable salt of infigratinib is a monophosphate salt. In some embodiments, the pharmaceutically acceptable salt of infigratinib is an anhydrous monophosphate salt. In some embodiments, the pharmaceutically acceptable salt of infigratinib is an anhydrous monophosphate salt in a polymorphic form characterized by a X-ray powder diffraction (XRPD) peak (2 Theta) at 15.0°±0.2° (and can include the other XRPD peaks of this form as described herein).

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration. In some embodiments, the pharmaceutical compositions disclosed herein are administered orally.

The pharmaceutical compositions provided herein may also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions provided herein may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions.

In certain embodiments, the pharmaceutical compositions provided herein are administered to the patient as a solid dosage form. In some embodiments, the solid dosage form is a capsule.

In certain embodiments, the compounds provided herein can be administered as the sole active agent, or they can be administered in combination with other active agents.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Methods of Use and Treatment

Cholangiocarcinoma is a rare, heterogeneous malignancy which originates from the neoplastic transformation of cholangiocytes into intrahepatic, perihilar, or distal extrahepatic tumors (Alpini et al., 2001).

In one aspect, provided herein are methods of treating cholangiocarcinoma in a patient in need thereof. In certain embodiments, cholangiocarcinoma is advanced or metastatic cholangiocarcinoma. In certain embodiments, the patient has progression of the cholangiocarcinoma after previous administration of another therapy.

In certain embodiments, provided herein are methods of treating advanced or metastatic cholangiocarcinoma in a patient in need thereof, comprising: administering an effective amount of infigratinib, or a pharmaceutically acceptable salt thereof, wherein the patient has progression of the cholangiocarcinoma after previous administration of another therapy.

In certain embodiments, the previous administration of another therapy is a therapy for treating advanced or metastatic cholangiocarcinoma. In some embodiments, the previous administration of another therapy is administration of a chemotherapeutic agent. In some embodiments, the previous administration of a chemotherapeutic agent is a gemcitabine-containing regimen. In some embodiments, the gemcitabine-containing regimen comprises gemcitabine. In some embodiments, the gemcitabine-containing regimen comprises gemcitabine and cisplatin.

In certain embodiments, the previous administration of another therapy is administration of another chemotherapeutic agent selected from the group consisting of 5-fluorouracil, gemcitabine, cisplatin, capecitabine, oxaliplatin, and combinations thereof.

In certain embodiments, the previous administration of another therapy is administration of a receptor tyrosine kinase inhibitor.

In certain embodiments, the receptor tyrosine kinase inhibitor is a selective non-covalently binding inhibitor of FGFR1, FGFR2 and/or FGFR3. In some embodiments, the selective non-covalently binding inhibitor of FGFR1, FGFR2 and/or FGFR3 is selected from the group consisting of pemigatinib, rogaratinib, derazantinib, Debio1347, AZD4547, and combinations thereof.

In certain embodiments, the receptor tyrosine kinase inhibitor is a selective non-covalently binding inhibitor of FGFR1, FGFR2, FGFR3 and/or FGFR4. In some embodiments, the selective non-covalently binding inhibitor of FGFR1, FGFR2, FGFR3 and/or FGFR4 is selected from the group consisting of erdafitinib, LY2874455, PRN 1371, ASP5878, and combinations thereof.

In certain embodiments, the receptor tyrosine kinase inhibitor is a selective covalently binding inhibitor of FGFR1, FGFR2, FGFR3 and/or FGFR4. In some embodiments, the selective covalently binding inhibitor of FGFR1, FGFR2, FGFR3 and/or FGFR4 is TAS120.

In certain embodiments, the receptor tyrosine kinase inhibitor is a non-selective tyrosine kinase inhibitor. In some embodiments, the non-selective tyrosine kinase inhibitor is selected from the group consisting of ponatinib, dovitinib, levatanib ACTB-1003, Ki8751, lucitinib, masitinib, mubritinib, nintedanib, orantinib, PD089828, and combinations thereof.

In certain embodiments, the previous administration of another therapy is administration of another selective FGFR inhibitor. In some embodiments, the another selective FGFR inhibitor is selected from the group consisting of pemigatinib, rogaratinib, derazantinib, AZD4547, Debio1347, ASP5878, erdafitinib, LY2874455, PRN1371, TAS120, and combinations thereof. In some embodiments, the another selective FGFR inhibitor is a selective covalently binding inhibitor. In some embodiments, the selective covalently binding inhibitor is TAS120. In some embodiments, the another selective FGFR inhibitor is a selective non-covalently binding inhibitor. In some embodiments, the selective non-covalently binding inhibitor is pemigatinib, rogaratinib, derazantinib, AZD4547, and combinations thereof.

In certain embodiments, the cholangiocarcinoma has a FGFR1 gene fusion, translocation or another genetic alteration. In some embodiments, the FGFR1 gene fusion comprises a FGFR1 gene fusion partner selected from the group consisting of BAG4, ERLIN2, NTM, FGFR1OP2, TACC3, and TRP.

In certain embodiments, the cholangiocarcinoma has a FGFR2 gene fusion, translocation or another genetic alteration. In some embodiments, the FGFR2 gene fusion comprises a FGFR2 gene fusion partner selected from the group consisting of 10Q26.13, AFF1, AFF3, AFF4, AHCYL1, ALDH1L2, ARFIP1, BAG4, BAIAP2L1, BICC1, C10orf118, C10orf68, C7, CASC15, CASP7, CCDC147, $CCDCl_6$, CELF2, CIT, COL14A1, CREB5, CREM, DNAJC12, ERLIN2, HOOK1, INA, KCTD1, KIAA1217, KIAA1598, KIAA1967, KIFC3, MGEA5, NCALD, NOL4, NPM1, NRAP, OFD1, OPTN, PARK2, PAWR, PCMI, PDHX, PHLDB2, PPAPDC1A, PPHLN1, RASAL2, SFMBT2, SLC45A3, SLMAP, SLMAP2, SORBS1, STK26, STK3, TACC1, TACC2, TACC3, TBC1D1, TEL, TFEC, TRA2B, UBQLN1, VCL, WAC, ZMYM4, and FGFROP2. In some embodiments, the FGFR2 gene fusion comprises a FGFR2 gene fusion partner selected from the group consisting of 10Q26.13, AFF1, AFF4, AHCYL1, ALDH1L2, ARFIP1, BICC1, C10orf118, C7, CCDC147, CCDC1$_6$, CELF2, CREB5, CREM, DNAJC12, HOOK1, KCTD1, KIAA1217, KIAA1598, KIFC3, MGEA5, NOL4, NRAP, OPTN, PARK2, PAWR, PCMI, PHLDB2, PPHLN1, RASAL2, SFMBT2, SLMAP, SLMAP2, SORBS1, STK26, STK3, TACC3, TBC1D1, TFEC, TRA2B, UBQLN1, VCL, WAC, and ZMYM4.

In certain embodiments, the cholangiocarcinoma has a FGFR3 gene fusion, translocation or another genetic alteration. In some embodiments, the FGFR3 gene fusion comprises a FGFR2 gene fusion partner selected from the group consisting of BAIAP2L1, JAKMIP1, TACC3, TNIP2, and WHSC1. In some embodiments, the FGFR3 gene fusion comprises a FGFR3 gene fusion partner, wherein the FGFR gene fusion partner is TACC3.

In certain embodiments, the patient undergoes molecular prescreening, for example using next generation sequencing, circulating tumor DNA analysis or a fluorescence in situ hybridization assay, to determine whether the cholangiocarcinoma has a FGFR1, FGFR2, or FGFR3 gene fusion, translocation or another genetic alteration. In some embodiments, the molecular prescreening occurs prior to administration of the effective amount of infigratinib or a pharmaceutically acceptable salt thereof. In some embodiments, the molecular prescreening to occurs prior to the previous administration of another therapy.

In certain embodiments, the cholangiocarcinoma has an FGFR1, FGFR2 and/or FGFR3 mutation. In some embodiments, the FGFR1, FGFR 2 and/or FGFR3 mutation is selected from the group consisting of FGFR1 G818R, FGFR1 K656E, FGFR1 N546K, FGFR1 R445W, FGFR1 T141R, FGFR2 A315T, FGFR2 C382R, FGFR2 D336N, FGFR2 D471N, FGFR2 E565A, FGFR2 I547V, FGFR2 K641R, FGFR2 K659E, FGFR2 K659M, FGFR2 L617V, FGFR2 N549H, FGFR2 N549K, FGFR2 N549S, FGFR2 N549Y, FGFR2 N550K, FGFR2 P253R, FGFR2 S252W, FGFR2 V395D, FGFR2 V564F, FGFR2 Y375C, FGFR3 A391E, FGFR3 D785Y, FGFR3 E627K, FGFR3 G370C, FGFR3 G380R, FGFR3 K650E, FGFR3 K650M, FGFR3 K650N, FGFR3 K650T, FGFR3 K652E, FGFR3 N540S, FGFR3 R248C, FGFR3 R399C, FGFR3 S131L, FGFR3 S249C, FGFR3 S371C, FGFR3 V555M, FGFR3 V677I, FGFR3 Y373C, FGFR4 D425N, FGFR4 R183S, FGFR4 R394Q, FGFR4 R610H, FGFR4 V510L, and combinations thereof. In some embodiments, the FGFR1, FGFR 2 and/or FGFR3 mutation is selected from the group consisting of FGFR1 N546K, FGFR1 K656E, FGFR2 S252W, FGFR2 P253R, FGFR2 A315T, FGFR2 Y375C, FGFR2 C382R, FGFR2 N549K, FGFR2 K659E, FGFR3 R248C, FGFR3 S249C, FGFR3 G370C, FGFR3 S371C, FGFR3 Y373C, FGFR3 G380R, FGFR3 K650E, FGFR3 K650M, and combinations thereof.

In certain embodiments, the cholangiocarcinoma has a FGFR1 gene fusion and a FGFR1 mutation. In certain embodiments, the cholangiocarcinoma has a FGFR1 gene fusion and a FGFR2 mutation. In certain embodiments, the cholangiocarcinoma has a FGFR1 gene fusion and a FGFR3 mutation.

In certain embodiments, the cholangiocarcinoma has a FGFR2 gene fusion and a FGFR1 mutation. In certain embodiments, the cholangiocarcinoma has a FGFR2 gene fusion and a FGFR2 mutation. In certain embodiments, the cholangiocarcinoma has a FGFR2 gene fusion and a FGFR3 mutation.

In certain embodiments, the cholangiocarcinoma has a FGFR3 gene fusion and a FGFR1 mutation. In certain embodiments, the cholangiocarcinoma has a FGFR3 gene fusion and a FGFR2 mutation. In certain embodiments, the cholangiocarcinoma has a FGFR3 gene fusion and a FGFR3 mutation.

In certain embodiments, the cholangiocarcinoma has amplification of FGFR1, FGFR2, and/or FGFR3.

In certain embodiments, administering an effective amount of infigratinib or a pharmaceutically acceptable salt thereof, comprises administering about 125 mg of infigratinib or a pharmaceutically acceptable salt thereof.

In certain embodiments, the effective amount of infigratinib or a pharmaceutically acceptable salt thereof, is administered to the patient once daily.

In certain embodiments, the effective amount of infigratinib, or a pharmaceutically acceptable salt thereof, is administered to the patient orally.

In certain embodiments, administering an effective amount of infigratinib, or a pharmaceutically acceptable salt thereof, comprises administering orally about 25 mg of infigratinib, or a pharmaceutically acceptable salt thereof, once daily.

In certain embodiments, administering an effective amount of infigratinib, or a pharmaceutically acceptable salt thereof, comprises administering orally about 50 mg of infigratinib, or a pharmaceutically acceptable salt thereof, once daily.

In certain embodiments, administering an effective amount of infigratinib, or a pharmaceutically acceptable salt thereof, comprises administering orally about 75 mg of infigratinib, or a pharmaceutically acceptable salt thereof, once daily.

In certain embodiments, administering an effective amount of infigratinib, or a pharmaceutically acceptable salt thereof, comprises administering orally about 100 mg of infigratinib, or a pharmaceutically acceptable salt thereof, once daily.

In certain embodiments, administering an effective amount of infigratinib, or a pharmaceutically acceptable salt thereof, comprises administering orally about 125 mg of infigratinib, or a pharmaceutically acceptable salt thereof, once daily.

In certain embodiments, administering an effective amount of infigratinib, or a pharmaceutically acceptable salt thereof comprises a 28 day cycle, wherein about 25 mg of infigratinib, or a pharmaceutically acceptable salt thereof, is administered once daily to the patient for 3 consecutive weeks (21 days), and subsequently no infigratinib is administered for 1 week (7 days).

In certain embodiments, administering an effective amount of infigratinib, or a pharmaceutically acceptable salt thereof comprises a 28 day cycle, wherein about 50 mg of infigratinib, or a pharmaceutically acceptable salt thereof, is administered once daily to the patient for 3 consecutive weeks (21 days), and subsequently no infigratinib is administered for 1 week (7 days).

In certain embodiments, administering an effective amount of infigratinib, or a pharmaceutically acceptable salt thereof comprises a 28 day cycle, wherein about 75 mg of infigratinib, or a pharmaceutically acceptable salt thereof, is administered once daily to the patient for 3 consecutive weeks (21 days), and subsequently no infigratinib is administered for 1 week (7 days).

In certain embodiments, administering an effective amount of infigratinib, or a pharmaceutically acceptable salt thereof comprises a 28 day cycle, wherein about 100 mg of infigratinib, or a pharmaceutically acceptable salt thereof, is administered once daily to the patient for 3 consecutive weeks (21 days), and subsequently no infigratinib is administered for 1 week (7 days).

In certain embodiments, administering an effective amount of infigratinib, or a pharmaceutically acceptable salt thereof comprises a 28 day cycle, wherein about 125 mg of infigratinib, or a pharmaceutically acceptable salt thereof, is administered once daily to the patient for 3 consecutive weeks (21 days), and subsequently no infigratinib is administered for 1 week (7 days).

In certain embodiments, the effective amount of infigratinib, or a pharmaceutically acceptable salt thereof is administered to the patient for two, three, four, five, six, seven, eight, nine, ten, eleven, or twelve consecutive 28-days cycles.

In certain embodiments, the about 125 mg of infigratinib, or a pharmaceutically acceptable salt thereof, is provided as a unit dose. In certain embodiments, the about 100 mg of infigratinib, or a pharmaceutically acceptable salt thereof, is provided as a unit dose. In certain embodiments, the about 75 mg of infigratinib, or a pharmaceutically acceptable salt thereof, is provided as a unit dose. In certain embodiments, the about 50 mg of infigratinib, or a pharmaceutically acceptable salt thereof, is provided as a unit dose. In certain embodiments, the about 25 mg of infigratinib, or a pharmaceutically acceptable salt thereof, is provided as a unit dose.

In some embodiments, the about 125 mg of infigratinib or a pharmaceutically acceptable salt thereof is provided as a unit dose. In some embodiments, the about 125 mg of infigratinib or a pharmaceutically acceptable salt thereof is provided as a 100 mg unit dose and a 25 mg unit dose. In some embodiments, the about 125 mg of infigratinib or a pharmaceutically acceptable salt thereof is provided as a 75 mg unit dose and a 50 mg unit dose.

In certain embodiments, the about 100 mg of infigratinib, or a pharmaceutically acceptable salt thereof, is provided as a 75 mg unit dose and a 25 mg unit dose. In some embodiments, the about 100 mg of infigratinib, or a pharmaceutically acceptable salt thereof, is provided as two 50 mg unit doses.

In certain embodiments, the about 75 mg of infigratinib, or a pharmaceutically acceptable salt thereof, is provided as a 50 mg unit dose and a 25 mg unit dose.

In certain embodiments, the about 50 mg of infigratinib, or a pharmaceutically acceptable salt thereof, is provided as two 25 mg unit doses.

In certain embodiments, the about 125 mg of infigratinib or a pharmaceutically acceptable salt thereof is administered orally to the patient. In certain embodiments, the about 100 mg of infigratinib or a pharmaceutically acceptable salt thereof is administered orally to the patient. In certain embodiments, the about 75 mg of infigratinib or a pharmaceutically acceptable salt thereof is administered orally to the patient. In certain embodiments, the about 50 mg of infigratinib or a pharmaceutically acceptable salt thereof is administered orally to the patient. In certain embodiments, the about 25 mg of infigratinib or a pharmaceutically acceptable salt thereof is administered orally to the patient.

In some embodiments, the method further comprises administering an effective amount of infigratinib or a pharmaceutically acceptable salt thereof, to the patient in need thereof in the fasted state. In some embodiments, the effective amount of infigratinib or a pharmaceutically acceptable salt thereof, should be administered to the patient in need thereof at least 1 hour before the patient consumes food. In some embodiments, the effective amount of infigratinib or a pharmaceutically acceptable salt thereof, should be administered to the patient in need thereof at least 2 hours after the patient consumes food.

In certain embodiments, the advanced or metastatic cholangiocarcinoma is histologically or cytologically confirmed. In some embodiments, the advanced or metastatic cholangiocarcinoma is histologically confirmed. In some embodiments, the advanced or metastatic cholangiocarcinoma is cytologically confirmed.

In certain embodiments, the methods include administrating an effective amount of a pharmaceutically acceptable salt of infigratinib to a patient in need thereof. In some embodiments, the pharmaceutically acceptable salt of infigratinib is a monophosphate salt. In some embodiments, the pharmaceutically acceptable salt of infigratinib is an anhydrous monophosphate salt. In some embodiments, the pharmaceutically acceptable salt of infigratinib is an anhydrous monophosphate salt in a polymorphic form characterized by a X-ray powder diffraction (XRPD) peak (2 Theta) at 15.0°±0.2°. In some embodiments, the polymorphic form of the anhydrous crystalline monophosphate salt of infigratinib is described herein.

In another aspect, provided herein are methods of treating advanced or metastatic cholangiocarcinoma in a patient in need thereof, comprising: administering any one of the pharmaceutical compositions disclosed herein, wherein the patient has progression of the cholangiocarcinoma after previous administration of another therapy.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Example 1: Synthesis of 3-(2,6-dichloro-3,5-dimethoxy-phenyl)-1-{6-4-(4-ethyl-piperazin-1-yl)-phenylaminol-pyrimidin-4-yl}-1-methyl-urea (infigratinib)

Step A: Synthesis of N-4-(4-ethyl-piperazin-1-yl)-phenyl)-N'-methyl-pyrimidine-4,6-diamine A mixture of 4-(4-ethylpiperazin-1-yl)-aniline (1 g, 4.88 mmol), (6-chloro-pyrimidin-4-yl)-methyl-amine (1.81 g, 12.68 mmol. 1.3 eq.), and 4N HCl in dioxane (15 mL) is heated in a sealed tube to 150° C. for 5 hours. The reaction mixture is concentrated, diluted with dichloromethane (DCM) and a saturated aqueous solution of sodium bicarbonate. The aqueous layer is separated and extracted with DCM. The organic phase is washed with brine, dried (sodium sulfate), filtered and concentrated. Purification of the residue by silica gel column chromatography (DCM/MeOH, 93:7) followed by trituration in diethyl ether affords the title compound as a white solid: ESI-MS: 313.2[MH]$^+$; $t_R$=1.10 min (gradient J); TLC: $R_f$=0.21 (DCM/MeOH, 93:7).

Step B: Synthesis of 4-(4-ethylpiperazin-1-yl)-aniline

A suspension of 1-ethyl-4-(4-nitro-phenyl)-piperazine (6.2 g, 26.35 mmol) and Raney Nickel (2 g) in MeOH (120 mL) is stirred for 7 hours at RT, under a hydrogen atmosphere. The reaction mixture is filtered through a pad of celite and concentrated to afford 5.3 g of the title compound as a violet solid: ESI-MS: 206.1 [MH]$^+$; TLC: R$_f$=0.15 (DCM/MeOH+1% NH$_3$$^{aq}$, 9:1).

Step C: Synthesis of 1-ethyl-4-(4-nitro-phenyl)-piperazine

A mixture of 1-bromo-4-nitrobenzene (6 g, 29.7 mmol) and 1-ethylpiperazine (7.6 mL, 59.4 mmol, 2 eq.) is heated to 80° C. for 15 hours. After cooling to RT, the reaction mixture is diluted with water and DCM/MeOH, 9:1. The aqueous layer is separated and extracted with DCM/MeOH, 9:1. The organic phase is washed with brine, dried (sodium sulfate), filtered and concentrated. Purification of the residue by silica gel column chromatography (DCM/MeOH+1% NH$_3$$^{aq}$, 9:1) affords 6.2 g of the title compound as a yellow solid: ESI-MS: 236.0 [MH]$^+$; t$_R$=2.35 min (purity: 100%, gradient J); TLC: R$_f$=0.50 (DCM/MeOH+1% NH$_3$$^{aq}$, 9:1).

Step D: Synthesis of (6-chloro-pyrimidin-4-yl)-methyl-amine

This material was prepared by a modified procedure published in the literature (J. Appl. Chem. 1955, 5, 358): To a suspension of commercially available 4,6-dichloropyrimidine (20 g, 131.6 mmol, 1.0 eq.) in isopropanol (60 mL) is added 33% methylamine in ethanol (40.1 mL, 328.9 mmol, 2.5 eq.) at such a rate that the internal temperature does not rise above 50° C. After completion of the addition the reaction mixture was stirred for 1 hour at room temperature. Then, water (50 mL) is added and the suspension formed is chilled in an ice bath to 5° C. The precipitated product is filtered off, washed with cold isopropanol/water 2:1 (45 mL) and water. The collected material is vacuum dried over night at 45° C. to afford the title compound as colorless powder: t$_R$=3.57 min (purity: >99%, gradient A), ESI-MS: 144.3/146.2 [MH]$^+$.

Step E: Synthesis of 3-(2,6-dichloro-3,5-dimethoxy-phenyl)-1-{6-4-(4-ethyl-piperazin-1-yl)-phenylaminol-pyrimidin-4-yl}-1-methyl-urea The title compound was prepared by adding 2,6-dichloro-3,5-dimethoxyphenyl-isocyanate (1.25 eq.) to a solution of N-4-(4-ethyl-piperazin-1-yl)-phenyl)-N'-methyl-pyrimidine-4,6-diamine (2.39 g, 7.7 mmol, 1 eq.) in toluene and stirring the reaction mixture for 1.5 hours at reflux. Purification of the crude product by silica gel column chromatography (DCM/MeOH+1% NH$_3$$^{aq}$, 95:5) affords the title compound as a white solid: ESI-MS: 560.0/561.9 [MH]$^+$; t$_R$=3.54 min (purity: 100%, gradient J); TLC: R$_f$=0.28 (DCM/MeOH+1% NH$_3$$^{aq}$, 95:5). Analysis: C$_{26}$H$_{31}$N$_7$O$_3$Cl$_2$, calc. C, 55.72%; H, 5.57%; N, 17.49%; 0, 8.56%; Cl, 12.65%. Found C, 55.96%: H, 5.84%: N, 17.17%; 0, 8.46%; Cl, 12.57%.

Example 2: Synthesis of the Monophosphate Salt Form A of 3-(2,6-dichloro-3,5-dimethoxy-phenyl)-1-{6-4-(4-ethyl-piperazin-1-yl)-phenylaminol-pyrimidin-4-yl}-1-methyl-urea (BGJ398)

To a round bottom flask was added 3-(2,6-dichloro-3,5-dimethoxyphenyl)-1-(6-4-(4-ethylpiperazin-1-yl)phenylaminol-pyrimidine-4-yl)-1-methyl-urea (134 g, 240 mmol) and isopropanol (IPA) (2000 mL). The suspension was stirred and heated to 50° C. and a solution of phosphoric acid (73.5 g, 750 mmol) in water (2000 mL) added to it portions. The mixture was stirred at 60° C. for 30 minutes and filtered through a polypropylene pad. The pad was washed with warm IPA/water (1:1, 200 mL) and the filtrates were combined. To this clear solution, IPA (6000 mL) was added and the mixture was stirred under reflux for 20 minutes, cooled slowly to room temperature (25° C.), and stirred for 24 hours. The white salt product was collected by filtration, washed with IPA (2×500 mL) and dried in the oven at 60° C. under reduced pressure for two days to provide the anhydrous crystalline monophosphate salt (110 g). Yield 70%. Purity>98% by HPLC. Analysis: C$_{26}$H$_{34}$N$_7$O$_7$Cl$_2$P, calc. C, 47.42%; H, 5.20%; N, 14.89%; O, 17.01%; Cl, 10.77%; P. 4.70%. Found C, 47.40%; H, 5.11%: N, 14.71%; O, 17.18%: Cl, 10.73%; P, 4.87%.

Example 3: Manufacturing Process for 25 mg, 100 mg, and 125 mg Dose Infigratinib Pharmaceutical Formulations In the following example, the manufacturing process is outlined for all exemplified dosage strengths.

The corresponding amounts of the ingredients are provided in the formulas under Examples 3.1, 3.2, and 3.3 below.

Manufacture of the Pharmaceutical Blend

Cellulose MK-GR, lactose (milled), infigratinib, cellulose HPM 603 and cross-linked polyvinylpyrrolidone (PVP-XL) are sequentially added into a vertical wet high-shear granulator (e.g., TK Fiedler (bottom driven, 65 L) with a granulator fill volume of about 45-50%, the five components are then mixed at an impeller setting of 60-270 rpm, preferably 150 rpm; and a chopper setting of 600-3000 rpm, preferably 1500 rpm, for about 5 min to obtain a dry blend.

Purified water is added as granulation liquid at rate of about 385 g/min for 7 min (adding up to about 2.7 kg of water) with a spray setting pressure of 1.5 bar (impeller setting of 60-270 rpm, preferably 150 rpm; and chopper settings of 600-3000 rpm, preferably 1500 rpm). The resulting granulation mixture is kneaded for about 3 min (impeller setting of 60-270 rpm, preferably 150 rpm; and chopper setting of 600-3000 rpm, preferably 1500 rpm). The kneaded granulation mass is screened through a 3.0 mm sieve using a Comil with 90-600 rpm. This process step is optional and may be omitted, but preferably this process step is performed.

The granules are dried in a fluidized bed dryer, e.g., Glatt GPCG 15/30 or equivalent, with an inlet air temperature of 55-65° C., preferably 60° C., a product temperature of about 30-40° C. and an inlet air volume of 300-1200 m$^3$/h to reach a drying endpoint of ≤2.2%.

The dried granules are screened through 800-1000 m in a Comil. The resulting dried and screened granules are also referred to herein as an inner phase.

The outer phase excipients PVP XL and Aerosil 200 are screened through 900-1000 m in a Comil with ca. 50-150 rpm and then combined with the inner phase in a suitable container (e.g., bin blender, turbula or equivalent) by mixing with 4-25 rpm, preferably 17 rpm for about 5 min (33-66% powder fill).

The solids are lubricated by the addition of 500 rpm screened magnesium stearate as an additional outer phase excipient by blending in a diffusion mixer (tumble) or bin blender (e.g., Bohle PM400, Turbula, or equivalent) for about 3 min at about 17 rpm, to obtain the final blend which is ready for capsule filling.

Manufacturing of the Capsule

The final blend is then filled into hard gelatin capsules (HGC) of size 0, 1, or 3 by encapsulation machines with dosing plate principle or with dosing tube (e.g., Hofliger & Karg GKF 330, Bosch GKF 1500, Zanasi 12 E. Zanasi 40 E) with encapsulation speeds of 10,000 up to 100,000 caps/h and without precompression. The weights of the capsules are controlled and the capsules dedusted.

Example 3.1

TABLE 1

Formula for 25 mg Dosage Strength

| Component | Composition per unit [%] | Composition per Unit [mg/unit] | Quantity per 173'016 units [kg/batch] |
|---|---|---|---|
| Infigratinib as monophosphate[a] | 37.18[a] | 29.38[a] | 5.084[a] |
| Cellulose MK-GR | 25.63 | 20.25 | 3.505 |
| Lactose milled | 29.43 | 23.25 | 4.024 |
| Cellulose HPM603 | 3.16 | 2.50 | 0.433 |
| Polyvinylpolypyrrolidon XL | 3.16 | 2.50 | 0.433 |
| Purified water[b] | | | |
| Total inner phase | | 77.88 mg | 13.48 kg |
| Polyvinylpolypyrrolidon XL | 0.10 | 0.08 | 0.0138 |
| Aerosil 200 | 0.13 | 0.10 | 0.0177 |
| Magnesium Stearate | 1.20 | 0.95 | 0.164 |
| Total final blend | 100% | 79.01 mg | 13.67 kg |
| Hard gelatin capsule, size 3 | | 48.00 mg | |
| Total capsule weight | | 127.01 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 3.2

TABLE 2

Formula for 100 mg Dosage Strength

| Component | Composition per unit [%] | Composition per Unit [mg/unit] | Quantity per 173'016 units [kg/batch] |
|---|---|---|---|
| Infigratinib as monophosphate[a] | 37.18[a] | 117.5[a] | 5.084[a] |
| Cellulose MK-GR | 25.63 | 81.0 | 3.505 |
| Lactose milled | 29.43 | 93.0 | 4.024 |
| Cellulose HPM603 | 3.16 | 10.0 | 0.433 |
| Polyvinylpolypyrrolidon XL | 3.16 | 10.0 | 0.433 |
| Purified water[b] | | | |
| Total inner phase | | 311.5 mg | 13.48 kg |
| Polyvinylpolypyrrolidon XL | 0.10 | 0.32 | 0.0138 |
| Aerosil 200 | 0.13 | 0.41 | 0.0177 |
| Magnesium Stearate | 1.20 | 3.80 | 0.164 |
| Total final blend | 100% | 316.03 mg | 13.67 kg |
| Hard gelatin capsule, size 1 | | 76.00 mg | |
| Total capsule weight | | 392.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 3.3

TABLE 3

Formula for 125 mg Dosage Strength

| Component | Composition per unit [%] | Composition per Unit [mg/unit] | Quantity per 173'016 units [kg/batch] |
|---|---|---|---|
| Infigratinib as monophosphate[a] | 37.18[a] | 146.875[a] | 5.084[a] |
| Cellulose MK-GR | 25.63 | 101.25 | 3.505 |
| Lactose milled | 29.43 | 116.25 | 4.024 |
| Cellulose HPM603 | 3.16 | 12.5 | 0.433 |
| Polyvinylpolypyrrolidon XL | 3.16 | 12.5 | 0.433 |
| Purified water[b] | | | |
| Total inner phase | | 389.4 mg | 13.48 kg |
| Polyvinylpolypyrrolidon XL | 0.10 | 0.40 | 0.0138 |
| Aerosil 200 | 0.13 | 0.513 | 0.0177 |
| Magnesium Stearate | 1.20 | 4.75 | 0.164 |
| Total final blend | 100% | 395.03 mg | 13.67 kg |
| Hard gelatin capsule, size 0 | | 96.00 mg | |
| Total capsule weight | | 491.0 mg | |

[a]The salt factor is 1.175. The drug substance quantity has to be adjusted if the content is ≤99.5%. Respective compensation is done by adjusting lactose content.
[b]The water used during granulation is removed in the process of drying.

Example 4: A Study of Oral Infigratinib (BGJ398) in Adult Patients with Advanced or Metastatic Cholangiocarcinoma Purpose and Rationale This study is designed to evaluate the efficacy of the targeted, selective pan-FGFR inhibitor BGJ398 when administered as a single agent to patients with genetically selected advanced or metastatic cholangiocarcinoma through estimation of the overall response rate.

Molecular characterization of these tumors at baseline and at the time of progression may allow for increased understanding of potential treatment combinations, as well as primary and acquired resistance mechanisms.

Primary Objective

Evaluate the efficacy of single agent BGJ398 in patients with advanced or metastatic cholangiocarcinoma with FGFR2 gene fusions or translocations or other FGFR genetic alterations as measured by overall response assessed by central imaging review according to RECIST v1.1 (Eisenhauer et al., 2009).

Secondary Objectives

Further evaluate the efficacy of single agent BGJ398 as measured by overall response assessed by investigator; progression free survival, best overall response, disease control assessed by investigator and by central imaging review as per RECIST v1.1; and overall survival.

Characterize the safety and tolerability of single agent BGJ398 by type, frequency, and severity of adverse events (AEs) and serious adverse events (SAEs).

Determine selected trough and 2-hr or 4-hr plasma concentrations of BGJ398 and its metabolites.

Characterize the pharmacokinetic profile of the 25 mg and 100 mg doses.

Study Design

This is a multi-center, open label, single arm phase II study evaluating BGJ398 anti-tumor activity in advanced or metastatic cholangiocarcinoma patients with FGFR genetic alterations. 125 mg of oral, monotherapy BGJ398 is administered once daily for the first 3 weeks (21 days) of each 28-day cycle. The starting dose of 125 mg may be reduced to 100 mg, 75 mg, or 50 mg. The treatment period begins on Cycle 1, Day 1, and continues until disease progression, unacceptable toxicity, withdrawal of informed consent, or death. Patients are evaluated for tumor response radiographically every 8 weeks until disease progression or discontinuation from study using RECIST v1.1 criteria.

Patient Population

Adult patients with histologically or cytologically confirmed advanced or metastatic cholangiocarcinoma with FGFR2 gene fusions or translocations or other FGFR genetic alteration who have evidence of radiologic progression following a cisplatin- and gemcitabine-containing regimen for advanced disease or a gemcitabine-containing regimen for those who are considered intolerant to cisplatin are enrolled. Up to approximately 160 adult patients over age 18, both male and female are enrolled. Three cohorts of patients comprise the study population:

Cohort 1: ~120 patients, 108 with FGFR2 gene fusions or translocations and 12 with other FGFR genetic alterations.

Cohort 2: ~20 patients with FGFR genetic alterations other than FGFR2 gene fusions or translocations.

Cohort 3: Up to ~20 patients with FGFR2 gene fusions or translocations who have received a prior FGFR inhibitor.

Main Inclusion Criteria

Patients with histologically or cytologically confirmed cholangiocarcinoma at the time of diagnosis. Patients with cancers of the gallbladder or ampulla of Vater are not eligible.

Written documentation of local or central laboratory determination of the following FGFR gene alterations:

Cohort 1: FGFR2 gene fusions or translocations.

Cohort 2: one of the following: (a) FGFR1 fusions or translocations, (b) FGFR3 fusions or translocations, or (c) FGFR1/2/3 mutation known to be an activating mutation and noted in Table 4.

TABLE 4

FGFR1/2/3 Allowed Mutations (Known Activating Mutations)

| FGFR Mutation | Functional Effect |
| --- | --- |
| FGFR1 N546K | Activating |
| FGFR1 K656E | Activating |
| FGFR2 S252W | Activating |
| FGFR2 P253R | Activating |
| FGFR2 A315T | Activating |
| FGFR2 Y375C | Activating |
| FGFR2 C382R | Activating |
| FGFR2 N549K | Activating |
| FGFR2 K659E | Activating |
| FGFR3 R248C | Activating |
| FGFR3 S249C | Activating |
| FGFR3 G370C | Activating |
| FGFR3 S371C | Activating |
| FGFR3 Y373C | Activating |
| FGFR3 G380R | Activating |
| FGFR3 K650E | Activating |
| FGFR3 K650M | Activating |

Cohort 3: FGFR2 gene fusions or translocations.

Patients must have received at least one prior regimen containing gemcitabine with or without cisplatin for advanced or metastatic disease. Patients should have had evidence of progressive disease following prior regimen, or if prior treatment discontinued due to toxicity must have continued evidence of measurable or evaluable disease.

An ECOG performance status≤1 (Patients with ECOG performance status of 2 may be considered on a case-by-case basis). The ECOG performance status is assessed as indicated in Table 5.

TABLE 5

ECOG Performance Status

| Grade | ECOG Status |
| --- | --- |
| 0 | Fully active, able to carry on all pre-disease performance without restriction. |
| 1 | Restricted in physically strenuous activity but ambulatory and able to carry out work of a light or sedentary nature (e.g., light housework, office work). |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |

Cohort 3 only: Documented prior treatment with FGFR inhibitor other than BGJ398/infigratinib.

Main Exclusion Criteria

Prior or current treatment with a MEK inhibitor (all cohorts), BGJ398/infigratinib (all cohorts), or selective FGFR inhibitor (Cohorts 1 and 2 only).

Current evidence of corneal or retinal disorder/keratopathy including, but not limited to, bullous/band keratopathy, corneal abrasion, inflammation/ulceration, keratoconjunctivitis, confirmed by ophthalmic examination.

History and/or current evidence of extensive tissue calcification including, but not limited to, the soft tissue, kidneys, intestine, myocardium, vascular system, and lung with the exception of calcified lymph nodes, minor pulmonary parenchymal calcifications, and asymptomatic coronary calcification.

Impairment of gastrointestinal (GI) function or GI disease that may significantly alter the absorption of oral BGJ398

(e.g., ulcerative diseases, uncontrolled nausea, vomiting, diarrhea, malabsorption syndrome, small bowel resection).

Current evidence of endocrine alterations of calcium/phosphate homeostasis, e.g., parathyroid disorders, history of parathyroidectomy, tumor lysis, tumoral calcinosis etc.

Concurrently receiving treatment with agents that are known strong inhibitors or inducers of CYP3A4. Medications which increase serum phosphorus and/or calcium concentration are excluded. Patients are not permitted to receive enzyme-inducing anti-epileptic drugs.

Cohort 3 only: Known existence of a V564F mutation in the FGFR2 gene.

Efficacy Assessments

Tumor response according to RECIST v1.1, and survival.

Safety Assessments

Adverse event (AE) reporting and changes from baseline in laboratory parameters, vital signs, ophthalmic assessment, and cardiac imaging.

Other Assessments

Pharmacokinetic assessment: Blood samples are collected for the measurement of the plasma concentrations of BGJ398 and its metabolites.

Biomarker assessment: Archival or newly obtained tumor samples are collected to explore mechanisms of resistance to cancer treatment through analysis of next generation DNA sequencing data from tumor samples at baseline and after the development of disease progression (whenever available).

Blood samples are collected at screening and throughout the study for cell free DNA analysis to explore correlation with genetic alterations in tumor tissue at baseline, clinical response and development of resistance.

Data Analysis

Data from participating centers in this protocol are combined, so that an adequate number of patients are available for analysis. Data are summarized with respect to demographic and baseline characteristics, efficacy and safety observations and measurements and all relevant PK and PD measurements. Categorical data are presented as frequencies and percentages. For continuous data, mean, standard deviation, median, 25th and 75th percentiles, minimum, and maximum are presented.

Results

Prior to starting the study treatment, Patient 5010004 had undertaken treatment with oral erdafitinib. Treatment with erdafitinib was discontinued after approximately 2 months due to radiological disease progression. That is, the patient's best response was progressive disease.

Patient 5010004 then started the study treatment approximately 2 months after discontinuing treatment with erdafitinib. During treatment with infigratinib, the patient's response was determined by follow-up assessments conducted by a local investigator per RECIST v1.1. It was determined that the patient had stable disease at the first 3 follow-up assessments, i.e., for at least about 4 months. The study treatment was discontinued for progressive disease after approximately 5 months. A summary of the study is shown in Table 6.

TABLE 6

Overall Response and Non-Target Lesion Response for Patient 5010004

| Evaluation Date | Study Day | Overall Response | Target Lesion % Change from Baseline | Non-Target Lesion Response | New Lesion |
|---|---|---|---|---|---|
| Sep. 26, 2019 | 0 | — | — | — | — |
| Nov. 18, 2019 | 54 | Stable disease | 18.33% | Non-CR[1]/Non-PD[2] | No |
| Dec. 17, 2019 | 83 | Stable disease | 16.33% | Non-CR/Non-PD | No |
| Jan. 13, 2020 | 110 | Stable disease | 16.33% | Non-CR/Non-PD | No |
| Feb. 25, 2020 | 153 | Progressive disease | 31.63% | Progressive disease | No |

[1]CR = complete response
[2]PD = progressive disease

Example 5: In Vivo Evaluation of the Antitumor Activity of Infigratinib and Erdafitinib Used as Single Agents in an FGFR3-Mutant Vex-MR086M1 Patient-Derived Ureter Carcinoma Xenograft Model Established in Nude Mice Objective Determine the antitumor activity of infigratinib used as single agent in comparison with the FGRF1-4 tyrosine kinase inhibitor erdafitinib in the FGFR3-mutated VEx-MR086M1 patient-derived ureter carcinoma xenograft model, developed in immunodeficient female mice.

Human Tumor Xenograft Model

The Vex-MR086M1 human tumor xenograft model was obtained from a metastatic lesion of a patient with bladder carcinoma having progressed under treatment with erdafitinib following initial response (Table 7). The patient's tumor and the Patient-Derived Xenograph (PDX) have a FGFR3 mutation (S249C). The PDX model was developed under treatment with erdafitinib (Carbosynth®) at 15 mg/kg, dosed 5 consecutive days per week.

TABLE 7

Human Tumor Xenograft Model Vex-MR086M1

| Organ/tissue or origin | Tumor type in patient | Origin in patient | Subtype (in PDX) | Cachexia | Latency (in day) | |
|---|---|---|---|---|---|---|
| | | | | | 60-200 mm³ | 1764 mm³ |
| Bladder | Carcinoma | Collar bone metastasis | / | No | Approx. 29 | Approx. 50 |

Animals and Maintenance Conditions

Outbred athymic (nu nu) female mice (HSD: Athymic Nude-Foxn1$^{nu}$) weighing 18-25 grams (ENVIGO, Gannat, France) were allocated to acclimate in the animal facility with access to food and water ad libitum for at least 6 days prior to manipulation (Table 8).

TABLE 8

Animal Characteristics

| Species | Strain | Supplier | Gender | Weight | Age at reception |
|---|---|---|---|---|---|
| Mouse (*Mus musculus*) | Athymic Nude - Foxn1$^{nu}$ | ENVIGO, France | Female | 18-25 g | 5 weeks |

Animal Husbandry

Mice were housed in groups of a maximum of 7 animals during acclimation period and a maximum of 6 animals during experimental phase. Mice were housed inside individually ventilated cages (IVC) of Polysulfone (PSU) plastic (mm 213 W×362 D×185 H, Allentown, USA) with sterilized and dust-free bedding cobs. Food and water were sterilized. Animals were housed under a light-dark cycle (14-hour circadian cycle of artificial light) and controlled room temperature and humidity. The environmental conditions were monitored and the data were retained in the Central Animal House Archives.

Diet and Water Supply

Drinking water was provided ad libitum. Each mouse was offered daily a complete pellet diet (150-SP-25, SAFE) throughout the study. The analytical certificate of animal food and water was retained at the CERFE premises.

Identification of Animals

All animals were weighed before each experiment and identified by a unique pattern for ear punch numbering system. Each cage was identified by a paper tag indicating: cage number, mice strain and number, tumor code, date of experiment.

Test Compound and Formulations

Infigratinib vehicle (50% 50 mM acetate buffer+50% PEG300 at pH4.6) for preparation of infigratinib and treatments of vehicle group, was prepared in two steps.

First step, preparation of 50 mM acetate buffer at pH 4.6+/−0.05: the required amount of sodium acetate trihydrate was weighted and dissolved in sterile deionized water. Then glacial acetate acid (1.5 ml for 1L) was added to the solution and the pH was adjusted to 4.6+/−0.5 with HCl 1N. Sterile deionized water was used to complete to the final volume.

Second steps, preparation of the 50% 50 mM acetate buffer+50% PEG300 at pH4.6 vehicle: the 50 mM acetate buffer at pH 4.6 was mixed with PEG300 (ratio 1:1, v/v) under magnetic stirring for at least 1 minutes.

The stock solution was stored at +4° C. for one month, in a light protected cabinet. One aliquot was made for each weeks of treatment.

Dosing solutions of 3 and 5 mg/ml free base (respectively 3.51 and 5.85 mg/ml salt form) of infigratinib (BGJ398) were prepared weighing the required amount of infigratinib, taking in consideration the ration salt form/free base of 1.17, then adding infiratinib vehicle (50% of 50 mM acetate buffer+50% PEG300 at pH4.6) under magnetic stirring (at least 15 minutes) until complete dissolution. Preparations were stored at +4° C. for 7 days, in a light protected cabinet.

HP-β-CD (Kleptose) 20% in sterile deionized water (for preparation of Erdafitinib) was prepared dissolving required amount of HP-β-CD in required amount of sterile deionized water under magnetic stirring. The stock solution was stored at +4° C. for one month, in a light protected cabinet.

Dosing solutions of 1.5 mg/ml of erdafitinib were prepared weighing the required amount of erdafitinib, then adding HP-β-CD 20% under magnetic stirring until complete dissolution. Preparations were stored at +4° C. for 7 days, in a light protected cabinet.

Tumorgraft Model Induction

Tumors of the same passage were transplanted subcutaneously onto 3-24 mice (donor mice, passage (n−1)). When these tumors reached 1470 to 1688 mm³, donor mice were sacrificed by cervical dislocation, tumors were aseptically excised and dissected. After removing necrotic areas, tumors were cut into fragments measuring approximately 20 mm³ and transferred in culture medium before grafting.

Fifty nine (59) mice were anaesthetized with 100 mg/kg ketamine hydrochloride and 10 mg/kg xylazine, and then skin was aseptized with a chlorhexidine solution, incised at the level of the interscapular region, and a 20 mm³ tumor fragment was placed in the subcutaneous tissue. Skin was closed with clips.

All mice from the same experiment were implanted on the same day.

Treatment Phase

In the study, 28 mice with VEx-MR086M1 established growing tumor (P9.1.1/0) between 62.5 and 196 mm³ were allocated, according to their tumor volume to give homogenous mean and median tumor volume in each treatment arm (Table 9). Treatments were randomly attributed to boxes housing up to 5 mice and were initiated 36 days post implantation of the tumor (47% inclusion rate). The study was terminated following 21 days after the start of treatment.

TABLE 9

Mice Groupings

| Group | Agent | Mean (mm³) | Median (mm³) | SEM |
|---|---|---|---|---|
| 1 | vehicle | 112.71 | 108 | 20.79 |
| 2 | Erdafitinib 15 mg/kg | 119.21 | 108 | 19.12 |
| 3 | Infigratinib 30 mg/kg | 119.21 | 108 | 19.12 |
| 4 | Infigratinib 50 mg/kg | 121.79 | 126 | 22.37 |

Tumor Measurement and Animal Observation

Tumor volume was evaluated by measuring perpendicular tumor diameters, with a caliper, three time a week during the treatment period.

All animals were weighed at the same time as tumor size measurement. A Relative Body Weight loss (RBW loss) was considered as adverse effect of the treatment.

Mice were observed every day for physical appearance, behavior and clinical changes.

All signs of illness, together with any behavioral change or reaction to treatment, were recorded for each animal.

Study Design

A total of 4 groups were used as summarized in Table 10. Each group initially included 7 mice.

In group 1, vehicle was administered at 10 ml/kg by per os route every day for 21 days (D0 to D21).

In group 2, erdafitinib was administered at 15 mg/kg (10 ml/kg) by per os route every day for 21 days (D0 to D21).

In groups 3 and 4, infigratinib was administered respectively at 30 and 50 mg/kg (10 ml/kg) by per os route every day for 21 days (D0 to D21).

All treatment doses were adjusted for body weight at time of dosing.

TABLE 10

Dose and Dose Schedules

| | | | 1 Drug/Testing Agent | | | |
|---|---|---|---|---|---|---|
| Gr. | N | Agent | Dose mg/kg | Route | Volume ml/kg | Schedule |
| 1 | 7 | Vehicle | — | PO | 10 | qdx21* |
| 2 | 7 | Erdafitinib | 15 | PO | 10 | qdx21* |
| 3 | 7 | Infigratinib | 30 | PO | 10 | qdx21* |
| 4 | 7 | Infigratinib | 50 | -PO | 10 | qdx21* |

Total: 28 mice
*qd x 21: daily dose for 21 consecutive days (e.g. from D 0 to D 20)

Actions Implemented in Case of Body Weight Loss or Adverse Event

During the treatment period, general alteration of behavior or clinical signs was notified to the sponsor as soon as possible (within 24 h on weekdays-within 48 h on weekends).

Depending on tumor volume, in case of:
body weight loss≥15% (tumor volume≤1 100 mm3) OR
body weight loss≥10% (tumor volume>1 100 mm³),
the sponsor was informed in the shortest delay (within 24 h on weekdays-within 48 h on weekends).

Then, the following actions are taken:
Treatment was stopped for the concerned animal; treatment was resumed if body weight loss<10%.
DietGel Recovery® was given for the entire group in which the body weight loss was observed and the corresponding animal was weighed every day until body weight loss<10%; DietGel Recovery® addition was stopped if body weight loss<10%.

Criteria for Ethical Sacrifice

Each animal was sacrificed immediately if one of the following conditions was met:
General alteration of behaviour or clinical signs
Tumor volume≥1764 mm³
Body weight loss (BWL) necessitating immediate intervention
Mouse bearing a tumor≤1 100 mm³:
BWL≥20% at any time compared to the weight on the day of enrollment
BWL≥15% maintained for 48 hours compared with the weight on the day of enrollment (2 days or 3 consecutive measurements).
Mouse bearing a tumor>1 100 mm³:
BWL≥15% at any time compared to the weight on the day of enrollment
BWL≥10% maintained for 48 hours compared with the weight on the day of enrollment (2 days or 3 consecutive measurements.

Endpoints Study Termination

Only mice reaching ethical sacrifice criteria were sacrificed at the appropriate time. Whole experimental group was ended at the end of the experimental period.

The endpoints for the experiment were:
a treatment phase of 3 weeks.

Tumor Sampling 4 tumors from extra mice were collected for FFPE and RNA-later® when tumors reach 500-847 mm³.

For each compound and each dose, fresh tumor samples were collected from all mice per group, at the end of the study or the time of ethical sacrifice (except during the weekend) for FFPE and RNA later (56 samples: 28 FFPE and 28 RNA later).

Tumor Sampling for FFPE

½ tumor was processed for FFPE: tumor was fixed in 10% formalin for 24 hrs and transferred in ethanol 70%, and then sent to Althisia for paraffin embedding (i.e. 28+4 FFPE tumor samples).

Exact sampling time, duration of formalin fixation and of storage in ethanol were noted for each tumor sampling.

The duration of tumor storage in ethanol 70% not exceeded 2 weeks.

Tumor samples were embedded in paraffin whole of split if their size does not allow them to fit in one standard histology cassette. In case of too large tumor, two cassettes were made.

The samples were dehydrated and impregnated in paraffin on Peloris (Leica) according to Althisia procedures as described below:

7 baths in ethanol at different concentrations and temperatures 3 baths in xylene at different concentrations and temperatures 3 baths in paraffin at 65° c. in vacuum atmosphere.

After processing, the samples were embedded in paraffin blocks (Diawax paraffin).

The dehydration cycle departure time was recorded.

Tumor RNA Sampling

½ tumor for RNA: tumor was cut into 4×4×1 mm fragments, transferred in RNA-later®, stored at 4° C. for 24 hours, then RNA-later® was removed and samples were transferred to −80° C. for storage.

Exact sampling times was noted for each sample (i.e. 28+4 RNA-later® samples).

Data Analysis—Data Processing

All raw data were recorded on appropriate forms bound in numbered registers, stored and processed by a computer system.

Day 0 was considered the day of inclusion. The days of the experiment were subsequently numbered according to this definition. The treatment period began on day 0.

Recordings are expressed as mean±standard error of the mean (m±sem).

Relative Body Weight (RBW) is calculated for each measurement by dividing the body weight by the body weight at the start of treatment.

Individual Body weight loss percent (% BWL)=100−($BW_X/BW_0$×100), where $BW_X$ is the BW at any day during the treatment and $BW_0$ is the BW on the day of inclusion.

Mean Body weight loss percent (% BWL)=100−(mean $BW_X$/mean $BW_0$×100), where $BW_X$ is the mean BW at any day during the treatment and $BW_0$ is the mean BW on the day of inclusion.

Mean Relative body weight curves were obtained by plotting the mean RBW against time for each experimental group. Delta relative body weights (relative body weights of treated group compared to relative body weights of control group) were used for statistical analysis.

The formula TV (mm$^3$)=[length (mm)×width (mm)$^2$]/2 is used, where the length and the width are the longest and the shortest diameters of the tumor, respectively.

Tumor growth curves were obtained by plotting the mean tumor volume in mm$^3$ against time for each experimental group. Delta tumor volumes (relative tumor volumes of treated group compared to relative tumor volumes of control group) were used for statistical analysis.

Individual tumor growth delays (TGD) was calculated as the time in days required for individual tumors to reach 3- to 5-fold the initial tumor volume. Median growth delay/group was calculated and reported in the tables.

The tumor growth delay index (TGDI) was calculated as the median growth delay in the treated group divided by the median growth delay in the control group.

The percentage ratio between the mean tumor volume of a treated group (T) and the mean tumor volume of the control group (C) was calculated.

The tumor growth rate was evaluated by the formula $DT/T_0$ where DT is the difference in tumour volume (TV) between the considered day and the day of enrolment and $T_0$ is mean TV at D0. Therefore, $DT/T_0<0$ means TV at Dxx is decreased compared to mean TV at D0, and $DT/T_0>0$ means TV at Dxx is increased compared to mean TV at D0. The results were expressed in percent in the tables ([$DT/T_0$]× 100) where Dxx is the day end of the control group. Regarding RECIST-like classification based on tumor volume measurements, we had previously defined 20%>[$DT/T_0$]×100>−30% as the range above or below which tumours were considered as progressor or regressor respectively. Statistical analysis was done for each measurement by Mann-Whitney non parametric comparison test. Each treated group was compared with control group.

Results—Tolerability Data, Clinical Observations

In this study mice were weighed three times a week during the experimental period.

In group 1, vehicle administered at 10 ml/kg by per os route every day for 21 days (D0 to D21) was well tolerated with 3.1% mean body weight loss on D13 and 10.1% of maximum individual body weight loss on D11. No relevant observable signs were reported during the experimental period.

In group 2, erdafitinib administered at 15 mg/kg (10 ml/kg) by per os route every day for 21 days (D0 to D21) was well tolerated except for 1 mouse with no mean body weight loss and 10.6% of maximum individual body weight loss on D17 (p<0.05 from D11 to D18). Due to BWL≥15% for mouse #16 on D17, DietGel Recovery® was given to the whole group on D17. No relevant observable signs were reported during the experimental period.

In group 3, infigratinib administered at 30 mg/kg (10 ml/kg) by per os route every day for 21 days (D0 to D21) was well tolerated with 2.1% mean body weight loss on D21 and 8.6% of maximum individual body weight loss on D18. All mice had hollow at the level of sternum from D13 to D21 (end of the study). Strain-specific modifiers of the hollow at the level of sternum characteristics cannot be excluded. No other clinical symptoms were reported.

In group 4, infigratinib administered at 50 mg/kg (10 ml/kg) by per os route every day for 21 days (D0 to D21) was tolerated with 10.3% mean body weight loss and 19.8% of maximum individual body weight loss on D18. The relative body weight of the infigratinib-treated mice in this group was not significantly different compared to the vehicle control group at each timepoint. Due to BWL≥15% for mouse #53 from D6 to D8 (sacrificed on D8 due to BWL≥15° % during 3 consecutive days), mouse #67 from D18 to D21 and for mouse #21 on D18 and D21, DietGel Recovery® was given to the whole group. Treatments were suspended from D6 to D8 (for mouse #53) from D18 to D20 (for mice #67 and #21). All mice had hollow at the level of sternum from D11 or D13 to D21 (end of the study). Strain-specific modifiers of the hollow at the level of sternum characteristics cannot be excluded. No other clinical symptoms were reported.

Antitumor Efficacy Data

Figure 2:
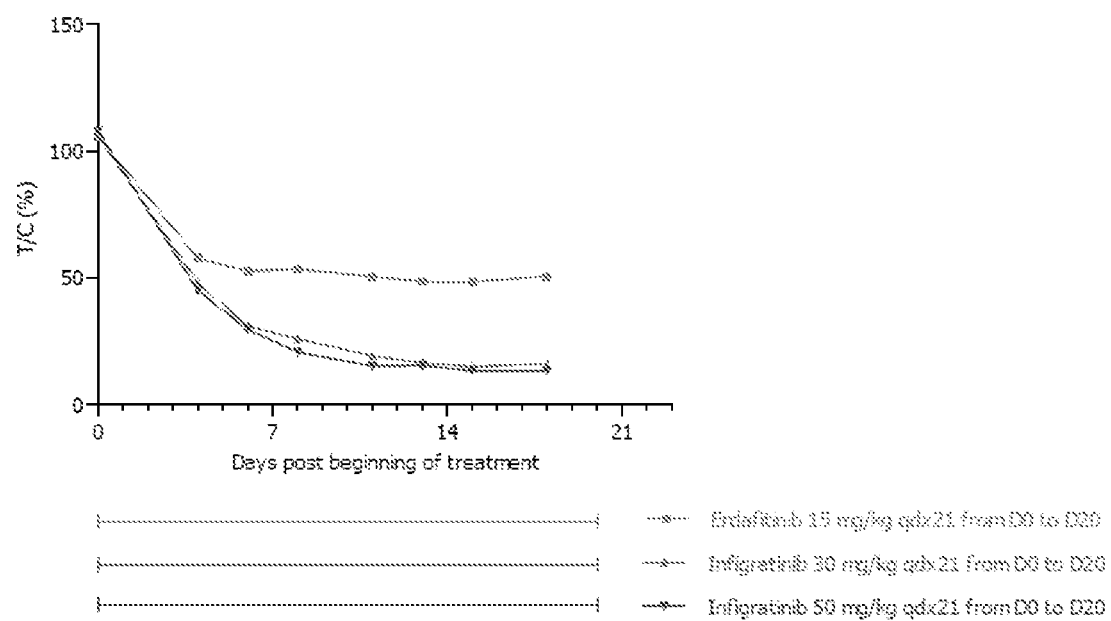
FIG. 2 is an overlay of the ratio of mean tumor volume in treated mice to mean tumor volume in control mice at the same timepoint (T/C %) curves for (i) erdafitinib 15 mg/kg qdx21, (ii) infigratinib 30 mg/kg qdx21, and (iii) infigratinib 50 mg/kg qdx21, in human Vex-MR086M1 ureter carcinoma xenograft model (XTS-2034), as further described in Example 5.

Tumor growth curves (mean tumor volume over time) are illustrated in FIG. 1. Percent T/C values for each treatment group are presented in Table 11 and illustrated in FIG. 2. Statistical analysis is shown in Table 12.

In this study mice were weighed three times a week during the experimental period.

In group 2, erdafitinib administered at 15 mg/kg (10 ml/kg) by per os route every day for 21 days (D0 to D21) induced statistically significant tumor growth inhibition compared to the control group (p<0.05 from D11 to D15; TGDI=1.71; best T/C=48.37% on D15 and ΔT/T0=465.31% on D18 (end of control group)).

In group 3, infigratinib administered at 30 mg/kg (10 ml/kg) by per os route every day for 21 days (D0 to D21) induced statistically significant tumor growth inhibition compared to the control group (p<0.05 on D6, p<0.01 from D8 to D18; TGDi>2.06, best T/C %=14.81% on D15 and ΔT/T0=77.83% on D18 (end of control group)). Infigratinib at 30 mg/kg showed higher tumor growth inhibition than erdafitinib at 15 mg/kg (p<0.05 from D11 to D21). The mean tumor volume of infigratinib-treated tumors was 3.2-fold lower than erdafitinib-treated tumors at D18 (End of Erdafitinib-treated group).

In group 4, infigratinib administered at 50 mg/kg (10 ml/kg) by per os route every day for 21 days (D0 to D21) induced statistically significant tumor growth inhibition compared to the control group (p<0.05 on D6, p<0.01 from D8 to D18; TGDi>2.06, best T/C %=13.13% on D15 and ΔT/T0=44.04% on D18 (end of control group)). Infigratinib at 50 mg/kg showed higher tumor growth inhibition than erdafitinib at 15 mg/kg (p<0.05 from D11 to D21). The mean tumor volume of infigratinib-treated tumors was 3.8-fold lower than erdafitinib-treated tumors at D18 (End of Erdafitinib-treated group).

Based on body weight data and clinical observations all compounds used as monotherapy were tolerated. However, infigratinib induced a slight and progressive BWL at the highest dose 50 mg/kg and one mouse was sacrificed due to BWL≥15% during 48 hours.

Erdafitinib monotherapy at 15 mg/kg, qdx21 show slight antitumor activity.

Infigratinib monotherapy at 30 and 50 mg/kg, qdx21 demonstrated statistically significant tumor growth inhibition. In the Vex-MR086M1 model, infigratinib demonstrated statistically significant antitumor activity of compared to erdafitinib.

TABLE 11

Anti-tumor activity of Infigratinib, alone and in comparison with Erdafitinib in the VEx-MR086M1 xenograft

| Gr. | Drug (1) | Dose (mg/kg) | Route | Schedule | Mean Tumor Volume at D 0 (mm$^3$) | median TGD × 5 (in days) | TGDI |
|---|---|---|---|---|---|---|---|
| G1 | Vehicle | — | PO | qdx21 | 112.7 | 10.19 | / |
| G2 | Erdafitinib | 15 | PO | qdx21 | 119.2 | 17.4 | 1.71 |
| G3 | Infigratinib | 30 | PO | qdx21 | 119.2 | >21 | >2.06 |
| G4 | Infigratinib | 50 | PO | qdx21 | 121.8 | >21 | >2.06 |

| Gr. | T/C % (at control group day end) | Best T/C % | at Day | DT/T$_0$ (at control group day end) | Best DT/T$_0$ | at Day | Mice Nb |
|---|---|---|---|---|---|---|---|
| G1 | / | / | / | 1083.27% | 123.26% | D 4 | 7 |
| G2 | 50.53% | 48.37% | D 15 | 465.31% | 21.69% | D 4 | 7 |
| G3 | 15.90% | 14.81% | D 15 | 77.83% | −16.66% | D 6 | 7 |
| G4 | 13.15% | 13.13% | D 15 | 44.04% | −31.91% | D 8 | 7 |

T/C = Mean tumor volume of treated mice/Mean tumor volume of control mice × 100 (calculated at the time of first ethical sacrifice in control group); TGD (Tumor Growth Delay) = time required for median tumor volume to reach D 0 tumor volume × 5; TGDI (Tumor Growth Delay Index) = TGD from treated/TGD from control mice; 100 × (ΔT/T0) where ΔT = difference in the mean tumor volume between Day 0 and Day XX (end of group), and T0 = mean tumor volume at D 0. Treatments started 36 days post implantation.

TABLE 12

Summary of Mann-Whitney analysis on tumor volume in the VEx-MR086M1 model

| MANN-WHITNEY TEST | DAY | 0 | 4 | 6 | 8 | 11 | 13 | 15 | 18 | STAT |
|---|---|---|---|---|---|---|---|---|---|---|
| Vehicle - qdx21 | vs Erdafitinib 15 qdx21 | ns | ns | ns | ns | * | * | * | ns | * |
| Vehicle - qdx21 | vs Infigratinib 30 qdx21 | ns | ns | * | ** | ** | ** | ** | ** | ** |
| Vehicle - qdx21 | vs Infigratinib 50 qdx21 | ns | ns | * | ** | ** | ** | ** | ** | ** |

| MANN-WHITNEY TEST | DAY | 0 | 4 | 6 | 8 | 11 | 13 | 15 | 18 | 21 | STAT |
|---|---|---|---|---|---|---|---|---|---|---|---|
| Erdafitinib 15 qdx21 | vs Vehicle - qdx21 | ns | ns | ns | ns | * | * | * | ns | | * |
| Erdafitinib 15 qdx21 | vs Infigratinib 30 qdx21 | ns | ns | ns | ns | * | * | * | * | * | * |
| Erdafitinib 15 qdx21 | vs Infigratinib 50 qdx21 | ns | ns | ns | ns | * | * | * | * | * | * |

Group comparisons were carried out using a Mann-Whitney nonparametric test between treated group and control group: ns = not significant,

* = P < 0.05,

** = P < 0.01, and

*** = P < 0.001.

Initial group size: 7 animals.

Example 6: In Vivo Evaluation of the Antitumor Activity of Infigratinib and Erdafitinib Used as Single Agents in an FGFR3-Mutant UREx-MR2057PD-AR Patient-Derived Ureter Carcinoma Xenograft Model Established in Nude Mice Objectives Determine antitumor activity of QED Therapeutics test compound infigratinib, an ATP-competitive, FGFR1-3 tyrosine kinase inhibitor, used as single agent and in comparison with the FGRF1-4 tyrosine kinase inhibitor erdafitinib (Erda) in the FGFR3-mutated UREx-MR2057PD-AR patient-derived ureter carcinoma xenograft model, developed in immunodeficient female mice.

The Human Tumor Xenograft Models

The UREx-MR2057PD-AR model was established from a metastatic lesion of a patient with urothelial carcinoma after progression under treatment with Erda. The treatment history before Erda is unknown but likely involved surgery and then non-targeted chemotherapy. The patient's tumor harbors an FGFR3 mutation, FGFR3 S249C (serine at amino acid 249 is mutated to cysteine), which is a known oncogenic mutation in the FGFR3 extracellular immunoglobulin-like domain that results in constitutive activation of the FGFR3 receptor. Infigratinib shows clinical efficacy in FGFR3 S249C-mutant urothelial carcinoma patients (Pal SK, Cancer Discovery, 2018).

Animals were housed under a light-dark cycle (14-hour circadian cycle of artificial light) and controlled room temperature and humidity. The environmental conditions were monitored and the data were retained in the Central Animal House Archives.

Diet and Water Supply

Drinking water was provided ad libitum. Each mouse was offered daily a complete pellet diet (150-SP-25, SAFE) throughout the study. The analytical certificate of animal food and water was retained at the CERFE premises.

Identification of Animals

All animals were weighed before each experiment and identified by a unique pattern for ear punch numbering system.

Each cage was identified by a paper tag indicating: cage number, mice strain and number, tumor code, date of experiment.

Test Compound and Formulations

Infigratinib vehicle (50% 50 mM acetate buffer+50% PEG300 at pH4.6) for preparation of infigratinib and treatments of vehicle group, was prepared in two steps.

First step, preparation of 50 mM acetate buffer at pH 4.6+/−0.05: the required amount of sodium acetate trihydrate was weighted and dissolved in sterile deionized water. Then glacial acetate acid (1.5 ml for 1L) was added to the solution and the pH was adjusted to 4.6+/−0.5 with HCl 1N. Sterile deionized water was used to complete to the final volume.

TABLE 13

Human Tumor Xenograft Model UREx-MR2057PD-AR

| Tumor code | Organ/tissue of origin | Tumor type in patient | Origin in patient | Subtype (in PDX) | Cachexia | Estrogen | Latency (in day) | |
|---|---|---|---|---|---|---|---|---|
| | | | | | | | 60-200 mm³ | 1764 mm³ |
| UREx-MR2057PD-AR* | Ureter | / | / | / | Yes | No | Approx. 12 | Approx. 33 |

*The UREx-MR2057PD-AR human tumor xenograft model was obtained from a patient with an urothelial carcinoma having progressed under treatment with erdafitinib following initial response. The erdafitinib-resistant patient's tumor and PDX model harbour a FGFR3 mutation (S249C). The PDX model was developed under treatment with erdafitinib (Carbosynth®) at 15 mg/kg, dosed 5 consecutive days per week Animals and Maintenance Conditions Outbred athymic (nu nu) female mice (HSD: Athymic Nude-Foxn1$^{nu}$) weighing 18-25 grams (EVIGO, Gannat, France) were allocated to acclimate in the animal facility with access to food and water ad libitum for at least 6 days prior to manipulation (Table 14).

TABLE 14

Animal Characteristics

| Species | Strain | Supplier | Gender | Weight | Age at reception |
|---|---|---|---|---|---|
| Mouse (Mus musculus) | Athymic Nude - Foxn1$^{nu}$ | ENVIGO, France | Female | 18-25 g | 5 weeks |

Animal Husbandry

Mice were housed in groups of a maximum of 7 animals during acclimation period and a maximum of 6 animals during experimental phase. Mice were housed inside individually ventilated cages (IVC) of Polysulfone (PSU) plastic (mm 213 W×362 D×185 H, Allentown, USA) with sterilized and dust-free bedding cobs. Food and water were sterilized.

Second steps, preparation of the 50% 50 mM acetate buffer+50% PEG300 at pH4.6 vehicle: the 50 mM acetate buffer at pH 4.6 was mixed with PEG300 (ratio 1:1, v/v) under magnetic stirring for at least 1 minutes.

The stock solution was stored at +4° C. for one month, in a light protected cabinet. One aliquot was made for each weeks of treatment.

Dosing solutions of 3 and 5 mg/ml free base (respectively 3.51 and 5.85 mg/ml salt form) of infigratinib (BGJ398) were prepared weighing the required amount of infigratinib, taking in consideration the ration salt form/free base of 1.17, then adding infiratinib vehicle (50% of 50 mM acetate buffer+50% PEG300 at pH 4.6) under magnetic stirring (at least 15 minutes) until complete dissolution. Preparations were stored at +4° C. for 7 days, in a light protected cabinet.

HP-β-CD (Kleptose) 20% in sterile deionized water (for preparation of Erdafitinib) was prepared dissolving required amount of HP-β-CD in required amount of sterile deionized water under magnetic stirring. The stock solution was stored at +4° C. for one month, in a light protected cabinet.

Dosing solutions of 1.5 mg/ml of erdafitinib were prepared weighing the required amount of erdafitinib, then adding HP-β-CD 20% under magnetic stirring until complete dissolution. Preparations were stored at +4° C. for 7 days, in a light protected cabinet.

Tumorgraft Model Induction

Tumors of the same passage were transplanted subcutaneously onto 3-24 mice (donor mice, passage (n−1)). When these tumors reached 1372 to 1568 mm³, donor mice were sacrificed by cervical dislocation, tumors were aseptically excised and dissected. After removing necrotic areas, tumors were cut into fragments measuring approximately 20 mm³ and transferred in culture medium before grafting.

Forty four (44) mice were anaesthetized with 100 mg/kg ketamine hydrochloride and 10 mg/kg xylazine, and then skin was aseptized with a chlorhexidine solution, incised at the level of the interscapular region, and a 20 mm³ tumor fragment was placed in the subcutaneous tissue. Skin was closed with clips.

All mice from the same experiment were implanted on the same day.

Treatment Phase

In the study, 32 mice with UREx-MR2057PD-AR established growing tumor (P9.1.1/0) between 62.5 and 171.15 mm³ were allocated, according to their tumor volume to give homogenous mean and median tumor volume in each treatment arm (Table 15). Treatments were randomly attributed to boxes housing up to 5 mice and were initiated 9 days post implantation of the tumor (75% inclusion rate). The study was terminated following 21 days after the start of treatment.

TABLE 15

Mice Groupings

| Group | Agent | Mean (mm³) | Median (mm³) | SEM |
|---|---|---|---|---|
| 1 | vehicle | 81.13 | 68.75 | 8.01 |
| 2 | Erdafitinib 15 mg/kg | 89.06 | 68.75 | 13.71 |
| 3 | Infigratinib 30 mg/kg | 84.94 | 68.75 | 13.52 |
| 4 | Infigratinib 50 mg/kg | 82.69 | 75.00 | 7.63 |

Tumor Measurement and Animal Observations

Tumor volume was evaluated by measuring perpendicular tumor diameters, with a caliper, three time a week during the treatment period.

All animals were weighed at the same time as tumor size measurement. A Relative Body Weight loss (RBW loss) was considered as adverse effect of the treatment.

Mice were observed every day for physical appearance, behavior and clinical changes.

All signs of illness, together with any behavioral change or reaction to treatment, were recorded for each animal.

Study Design

A total of 4 groups were used as summarized in Table 16. Each group initially included 8 mice.

In group 1, vehicle was administered at 10 ml/kg by per os route every day for 21 days (D0 to D21).

In group 2, erdafitinib was administered at 15 mg/kg (10 ml/kg) by per os route every day for 21 days (D0 to D21).

In groups 3 and 4, infigratinib was administered respectively at 30 and 50 mg/kg (10 ml/kg) by per os route every day for 21 days (D0 to D21).

All treatment doses were adjusted for body weight at time of dosing.

TABLE 16

Dose and dose schedules

| | | | 1 Drug/Testing Agent | | | |
|---|---|---|---|---|---|---|
| Gr. | N | Agent | Dose mg/kg | Route | Volume ml/kg | Schedule |
| 1 | 8 | Vehicle | — | PO | 10 | qdx21* |
| 2 | 8 | Erdafitinib | 15 | PO | 10 | qdx21* |
| 3 | 8 | Infigratinib | 30 | PO | 10 | qdx21* |
| 4 | 8 | Infigratinib | 50 | -PO | 10 | qdx21* |

Total: 32 mice
*qd x 21: daily dose for 21 consecutive days (e.g. from D 0 to D 20)

Actions Implemented in Case of Body Weight Loss or Adverse Event

During the treatment period, general alteration of behavior or clinical signs was notified to the sponsor as soon as possible (within 24 h on weekdays-within 48 h on weekends).

Depending on tumor volume, in case of:
body weight loss≥15% (tumor volume≤1 100 mm³) OR body weight loss≥10% (tumor volume≥1 100 mm³), the sponsor was informed in the shortest delay (within 24 h on weekdays-within 48 h on weekends).

Then, the following actions are taken:
Treatment was stopped for the concerned animal; treatment was resumed if body weight loss<10%.
DietGel Recovery® was given for the entire group in which the body weight loss was observed and the corresponding animal was weighed every day until body weight loss<10%; DietGel Recovery® addition was stopped if body weight loss<10%.

Criteria for Ethical Sacrifice

Each animal was sacrificed immediately if one of the following conditions was met:
General alteration of behaviour or clinical signs
Tumor volume≥1764 mm³
Body weight loss (BWL) necessitating immediate intervention
Mouse bearing a tumor≤1 100 mm³:
BWL≥20% at any time compared to the weight on the day of enrollment
BWL≥15% maintained for 48 hours compared with the weight on the day of enrollment (2 days or 3 consecutive measurements).
Mouse bearing a tumor>1 100 mm³:
BWL≥15% at any time compared to the weight on the day of enrollment
BWL≥10% maintained for 48 hours compared with the weight on the day of enrollment (2 days or 3 consecutive measurements.

End Points/Study Termination

Only mice reaching ethical sacrifice criteria were sacrificed at the appropriate time. Whole experimental group was ended at the end of the experimental period.

The endpoints for the experiment were:
a treatment phase of 3 weeks.

Tumor Sampling 5 tumors from extra mice were collected for FFPE and RNA Later® when tumors reach 500-726 mm³.

For each compound and each dose, fresh tumor samples were collected from all mice per group, at the end of the study or the time of ethical sacrifice (except during the week end) for FFPE and RNA later (64 samples: 32 FFPE and 32 RNA later).

Tumor Sampling for FFPE

½ tumor was processed for FFPE: tumor was fixed in 10% formalin for 24 hrs and transferred in ethanol 70%, and then sent to Althisia for paraffin embedding (i.e. 32+5 FFPE tumor samples).

Exact sampling time, duration of formalin fixation and of storage in ethanol were noted for each tumor sampling.

The duration of tumor storage in ethanol 70% not exceeded 2 weeks.

Tumor samples were embedded in paraffin whole of split if their size does not allow them to fit in one standard histology cassette. In case of too large tumor, two cassettes were made.

The samples were dehydrated and impregnated in paraffin on Peloris (Leica) according to Althisia procedures as described below:
- 7 baths in ethanol at different concentrations and temperatures
- 3 baths in xylene at different concentrations and temperatures
- 3 baths in paraffin at 65° c. in vacuum atmosphere.
- After processing, the samples were embedded in paraffin blocks (Diawax paraffin).

The dehydration cycle departure time was recorded.

Tumor RNA Sampling

½ tumor for RNA: tumor was cut into 4×4×1 mm fragments, transferred in RNAlater, stored at 4° C. for 24 hours, then RNAlater was removed and samples were transferred to −80° C. for storage.

Exact sampling times was noted for each sample (i.e. 32+5 RNA later samples).

Data Analysis—Data Processing

All raw data were recorded on appropriate forms bound in numbered registers, stored and processed by a computer system.

Day 0 was considered the day of inclusion. The days of the experiment were subsequently numbered according to this definition. The treatment period began on day 0.

Recordings are expressed as mean±standard error of the mean (m±sem).

Relative Body Weight (RBW) is calculated for each measurement by dividing the body weight by the body weight at the start of treatment.

Individual Body weight loss percent (% BWL)=100−($BW_X/BW_0 \times 100$), where $BW_X$ is the BW at any day during the treatment and $BW_0$ is the BW on the day of inclusion.

Mean Body weight loss percent (% BWL)=100−(mean $BW_X$/mean $BW_0 \times 100$), where $BW_X$ is the mean BW at any day during the treatment and $BW_0$ is the mean BW on the day of inclusion.

Mean Relative body weight curves were obtained by plotting the mean RBW against time for each experimental group. Delta relative body weights (relative body weights of treated group compared to relative body weights of control group) were used for statistical analysis.

The formula TV (mm$^3$)=[length (mm)×width (mm)$^2$]/2 is used, where the length and the width are the longest and the shortest diameters of the tumor, respectively.

Tumor growth curves were obtained by plotting the mean tumor volume in mm$^3$ against time for each experimental group. Delta tumor volumes (relative tumor volumes of treated group compared to relative tumor volumes of control group) were used for statistical analysis.

Individual tumor growth delays (TGD) was calculated as the time in days required for individual tumors to reach 3- to 5-fold the initial tumor volume. Median growth delay/group was calculated and reported in the tables.

The tumor growth delay index (TGDI) was calculated as the median growth delay in the treated group divided by the median growth delay in the control group.

The percentage ratio between the mean tumor volume of a treated group (T) and the mean tumor volume of the control group (C) was calculated.

The tumor growth rate was evaluated by the formula [Ty/Tx]−1 where Ty is mean tumor volume at the considered day and Tx is mean TV at DX. "−1" is used to compare with the day of enrollment. Therefore, if [Ty/Tx]−1<1 so mean TV at DY is decreased compared to mean TV at DX, and if [Ty/Tx]−1>1 so mean TV at DY is increased compared to mean TV at DX. The results were expressed in percent in the tables.

Statistical analysis was done for each measurement by Mann-Whitney non parametric comparison test. Each treated group was compared with control group.

Results—Tolerability Data, Clinical Observations

In this study mice were weighed three times a week during the experimental period.

In group 1, vehicle administered at 10 ml/kg by per os route every day for 21 days (D0 to D21) was well tolerated with no maximum mean body weight loss and 1.2% of maximum individual body weight loss on D3. No relevant observable signs were reported during the experimental period.

In group 2, erdafitinib administered at 15 mg/kg (10 ml/kg) by per os route every day for 21 days (D0 to D21) was well tolerated with no maximum mean body weight loss and 4.9% of maximum individual body weight loss on D3. No relevant observable signs were reported during the experimental period.

In group 3, infigratinib administered at 30 mg/kg (10 ml/kg) by per os route every day for 21 days (D0 to D21) was well tolerated with no mean body weight loss and 3.5% of maximum individual body weight loss on D3. All mice had hollow at the level of sternum from D15 to D21 (end of the study). Strain-specific modifiers of the hollow at the level of sternum characteristic cannot be excluded. No other clinical symptoms were reported.

In group 4, infigratinib administered at 50 mg/kg (10 ml/kg) by per os route every day for 21 days (D0 to D21) was tolerated with 6.6% mean body weight loss and 17.8% of maximum individual body weight loss on D21 (p<0.001 from D17 to D19). Due to BWL>15% for mouse #32 on D19, DietGel Recovery® was given to the whole group and treatments were suspended from D19 to D21. All mice had hollow at the level of sternum from D15 to D21 (end of the study). Strain-specific modifiers of the hollow at the level of sternum characteristic cannot be excluded. No other clinical symptoms were reported.

Results—Antitumor Efficacy Data

Figure 3:
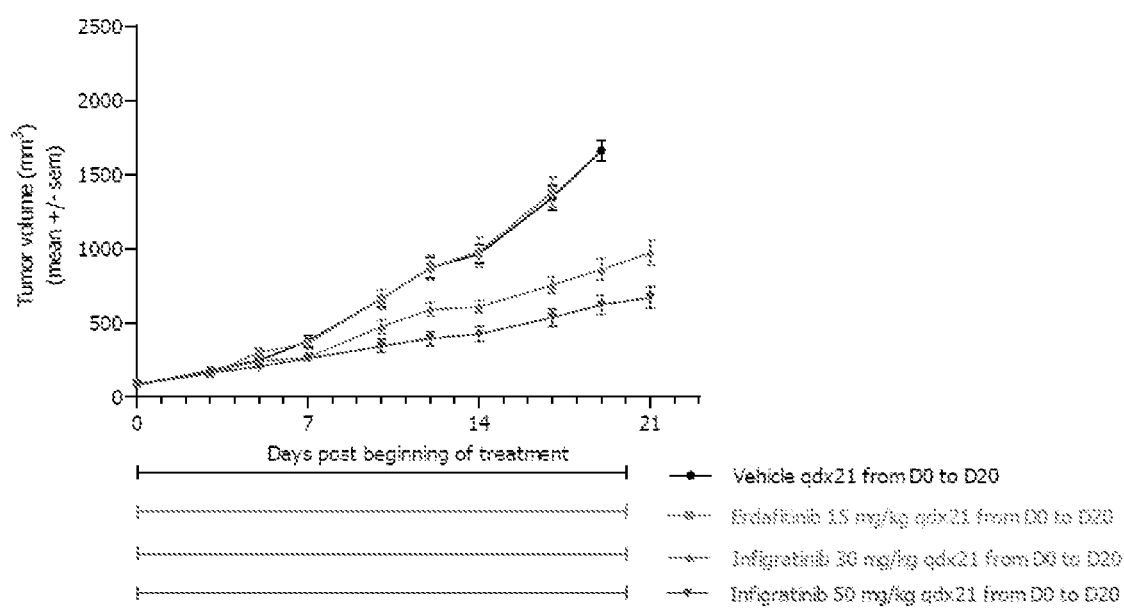
FIG. 3 is an overlay of tumor growth curves (mean tumor volume over time) for (i) vehicle qdx21, (ii) erdafitinib 15 mg/kg qdx21, (iii) infigratinib 30 mg/kg qdx21, and (iv) infigratinib 50 mg/kg qdx21, in human UREx-MR2057PD-AR ureter carcinoma xenograft model (XTS-2033), as further described in Example 6.
Figure 4:
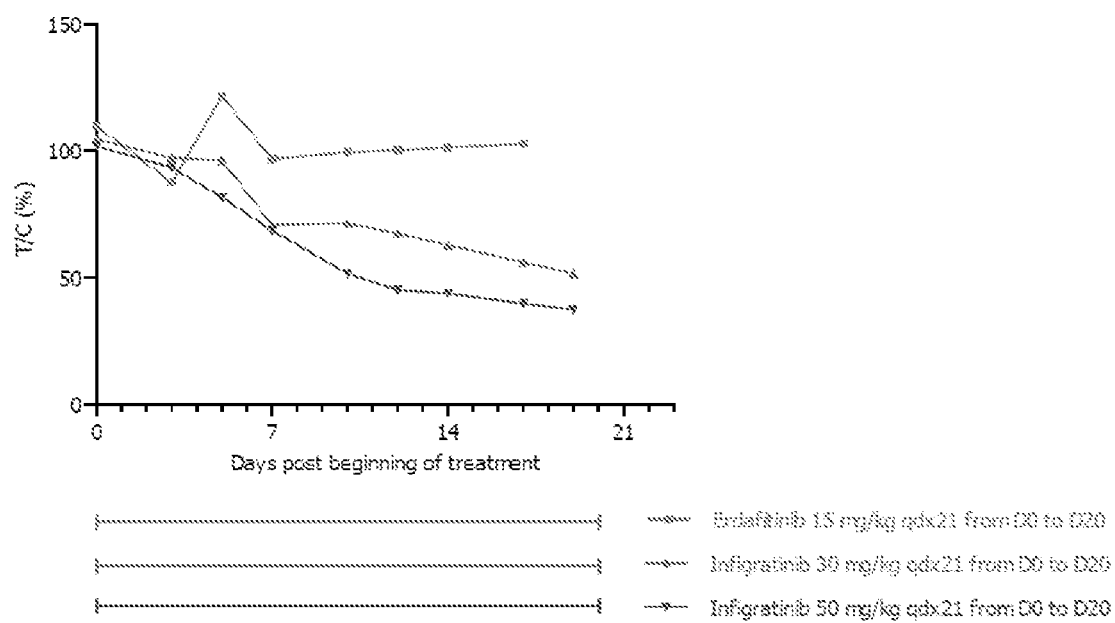
FIG. 4 is an overlay of T/C % curves for (i) erdafitinib 15 mg/kg qdx21, (ii) infigratinib 30 mg/kg qdx21, and (iii) infigratinib 50 mg/kg qdx21, in human UREx-MR2057PD-AR ureter carcinoma xenograft model (XTS-2034), as further described in Example 6.

Tumor growth curves (mean tumor volume over time) are illustrated in FIG. 3. Percent T/C values for each treatment group are presented in Table 17 and illustrated in FIG. 4. Statistical analysis is shown in Table 18.

In this study mice were weighed three times a week during the experimental period.

In group 2, erdafitinib administered at 15 mg/kg (10 ml/kg) by per os route every day for 21 days (D0 to D21) did not demonstrate any statistically significant tumor growth inhibition compared to the control group (TGDI=1.01; best T/C=87.71% on D3 and ΔT/T0=1450.67% on D17 (end of the group)).

In group 3, infigratinib administered at 30 mg/kg (10 ml/kg) by per os route every day for 21 days (D0 to D21) induced statistically significant tumor growth inhibition compared to the control group (p<0.05 from D7 to D12, p<0.01 from D14 to D17 and p<0.001 on D19; TGDi=1.20, best T/C %=51.66% on D19 and ΔT/T0=909.42% on D19 (end of control group)).

In group 4, infigratinib administered at 50 mg/kg (10 ml/kg) by per os route every day for 21 days (D0 to D21) induced statistically significant tumor growth inhibition compared to the control group (p<0.05 on D5, p<0.01 from D7 to D12 and p<0.001 from D14 to D19; TGDi=1.79, best T/C %=37.38% on D19 and ΔT/T0=650.26% on D19 (end of control group)). Infigratinib at 50 mg/kg showed higher tumor growth inhibition than at 30 mg/kg (p<0.05 from D10 to D21).

Based on body weight data and clinical observations all compounds used as monotherapy were tolerated. However, infigratinib induced a slight but statistically significant and progressive BWL at the highest dose 50 mg/kg.

Erdafitinib monotherapy at 15 mg/kg, qdx21 did not show any antitumor activity.

Infigratinib at 30 and 50 mg/kg, qdx21 administered as monotherapy demonstrated statistically significant and dose-dependent tumor growth inhibition (p<0.05 from D10 to D21 between infigratinib dosed at 30 and 50 mg/kg).

TABLE 17

Anti-tumor activity of Infigratinib, alone and in comparison with Erdafitinib in the UREx-MR2057PD-AR xenograft

| Gr. | Drug (1) | Dose (mg/kg) | Route | Schedule | Mean Tumor Volume at D 0 (mm$^3$) | median TGD × 5 (in days) | TGDI |
|---|---|---|---|---|---|---|---|
| G1 | Vehicle | — | PO | qdx21 | 81.1 | 7.43 | / |
| G2 | Erdafitinib | 15 | PO | qdx21 | 89.1 | 7.52 | 1.01 |
| G3 | Infigratinib | 30 | PO | qdx21 | 84.9 | 8.93 | 1.2 |
| G4 | Infigratinib | 50 | PO | qdx21 | 82.7 | 13.28 | 1.79 |

| Gr. | T/C % (at control group day end) | Best T/C % | at Day | DT/T$_0$ (at control group day end) | Best DT/T$_0$ | at Day | Mice Nb |
|---|---|---|---|---|---|---|---|
| G1 | / | / | / | 1945.69% | 115.72% | D 3 | 8 |
| G2 | 102.85% | 87.71% | D 3 | / | 72.35% | D 3 | 8 |
| G3 | 51.66% | 51.66% | D 19 | 909.42% | 100.37% | D 3 | 8 |
| G4 | 37.38% | 37.38% | D 19 | 650.26% | 97.81% | D 3 | 8 |

T/C = Mean tumor volume of treated mice/Mean tumor volume of control mice × 100 (calculated at the time of first ethical sacrifice in control group); TGD (Tumor Growth Delay) = time required for the median tumor volume to reach D 0 tumor volume × 5; TGDI (Tumor Growth Delay Index) = TGD from treated/TGD from control mice; 100 × (ΔT/T0) where ΔT = difference in the mean tumor volume between Day 0 and Day XX (end of group), and T0 = mean tumor volume at D 0. Treatments started 9 days post implantation.

TABLE 18

Summary of Mann-Whitney analysis on tumor volume in the UREx-MR2057PD-AR model

| MANN-WHITNEY TEST | DAY | 0 | 3 | 5 | 7 | 10 | 12 | 14 | 17 | 19 | STAT |
|---|---|---|---|---|---|---|---|---|---|---|---|
| Vehicle - qdx21 | vs Erdafitinib 15 qdx21 | ns | ns | ns | ns | ns | ns | ns | ns | | ns |
| Vehicle - qdx21 | vs Infigratinib 30 qdx21 | ns | ns | ns | * | * | * | ** | ** | *** | ** |
| Vehicle - qdx21 | vs Infigratinib 50 qdx21 | ns | ns | * | ** | ** | ** | *** | *** | *** | *** |

| MANN-WHITNEY TEST | DAY | 0 | 3 | 5 | 7 | 10 | 12 | 14 | 17 | 19 | 21 | STAT |
|---|---|---|---|---|---|---|---|---|---|---|---|---|
| Infigratinib 30 qdx21 | vs Erdafitinib 15 qdx21 | ns | ns | ns | ns | ns | * | ** | *** | | | *** |
| Infigratinib 30 qdx21 | vs Vehicle - qdx21 | ns | ns | ns | * | * | * | ** | ** | *** | | ** |
| Infigratinib 30 qdx21 | vs Infigratinib 50 qdx21 | ns | ns | ns | ns | * | * | * | * | * | * | * |

Group comparisons were carried out using a Mann-Whitney nonparametric test between treated group and control group: ns = not significant,
* = P < 0.05,
** = P < 0.01, and
*** = P < 0.001.
Initial group size: 8 animals.

INCORPORATION BY REFERENCE

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method for treating advanced or metastatic cholangiocarcinoma in a subject in need thereof, comprising:
administering infigratinib monophosphate salt once daily in an amount of about 50, 75, 100, or 125 milligrams (mg) by weight in its free base form,
wherein the subject has progression of the cholangiocarcinoma after previous administration of another therapy; the cholangiocarcinoma has an FGFR2 gene fusion, translocation, or another genetic alteration; the about 125 mg amount of infigratinib monophosphate salt is provided as a 100 mg unit dose and a 25 mg unit dose, each by weight in its free base form; the infigratinib monophosphate salt is administered at least 1 hour before the subject consumes food or at least 2 hours after the subject has consumed food; and administering the infigratinib monophosphate salt comprises a 28-day cycle in which the infigratinib monophosphate salt is administered to the subject for 3 consecutive weeks, and no infigratinib monophosphate salt is administered for 1 week.

2. The method of claim 1, wherein the previous administration of another therapy is a therapy for advanced or metastatic cholangiocarcinoma.

3. The method of claim 1, wherein the previous administration of another therapy is an administration of a chemotherapeutic agent.

4. The method of claim 3, wherein the previous administration of a chemotherapeutic agent is a gemcitabine-containing regimen.

5. The method of claim 1, wherein the cholangiocarcinoma has a FGFR1 and/or a FGFR3 gene fusion, translocation, or other genetic alteration.

6. The method of claim 1, wherein the FGFR2 gene fusion comprises a FGFR2 gene fusion partner selected from the group consisting of 10Q26.13, AFF1, AFF4, AHCYL1, ALDH1L2, ARFIP1, BICC1, C10orf118, C7, CCDC147, CCDC6, CELF2, CREB5, CREM, DNAJC12, HOOK1, KCTD1, KIAA1217, KIAA1598, KIFC3, MGEA5, NOL4, NRAP, OPTN, PARK2, PAWR, PCMI, PHLDB2, PPHLN1, RASAL2, SFMBT2, SLMAP, SLMAP2, SORBS1, STK26, STK3, TACC3, TBC1D1, TFEC, TRA2B, UBQLN1, VCL, WAC, and ZMYM4.

7. The method of claim 1, wherein the advanced or metastatic cholangiocarcinoma is histologically or cytologically confirmed.

8. The method of claim 1, wherein the cholangiocarcinoma has a FGFR1, a FGFR2 and/or a FGFR3 mutation.

9. The method of claim 8, wherein the FGFR1, FGFR2, and/or FGFR3 mutation is selected from the group consisting of FGFR1 G818R, FGFR1 K656E, FGFR1 N546K, FGFR1 R445W, FGFR1 T141R, FGFR2 A315T, FGFR2 C382R, FGFR2 D336N, FGFR2 D471N, FGFR2 E565A, FGFR2 1547V, FGFR2 K641R, FGFR2 K659E, FGFR2 K659M, FGFR2 L617V, FGFR2 N549H, FGFR2 N549K, FGFR2 N549S, FGFR2 N549Y, FGFR2 N550K, FGFR2 P253R, FGFR2 S252W, FGFR2 V395D, FGFR2 V564F, FGFR2 Y375C, FGFR3 A391E, FGFR3 D785Y, FGFR3 E627K, FGFR3 G370C, FGFR3 G380R, FGFR3 K650E, FGFR3 K650M, FGFR3 K650N, FGFR3 K650T, FGFR3 K652E, FGFR3 N540S, FGFR3R248C, FGFR3 R399C, FGFR3 S131L, FGFR3 S249C, FGFR3 S371C, FGFR3 V555M, FGFR3 V677I, FGFR3 Y373C, FGFR4 D425N, FGFR4 R183S, FGFR4R394Q, FGFR4 R610H, FGFR4 V510L, and a combination thereof.

10. The method of claim 1, wherein the cholangiocarcinoma has amplification of FGFR1, FGFR2, and/or FGFR3.

11. The method of claim 1, wherein the previous administration of another therapy is administration of a receptor tyrosine kinase inhibitor.

12. The method of claim 11, wherein the receptor tyrosine kinase inhibitor is a selective inhibitor of FGFR1, FGFR2, FGFR3, and/or FGFR4.

13. The method of claim 12, wherein the selective inhibitor of FGFR1, FGFR2, FGFR3, and/or FGFR4 is selected from the group consisting of pemigatinib, rogaratinib, derazantinib, Debio1347, AZD4547, erdafitinib, LY2874455, PRN 1371, ASP5878, TAS120, and a combination thereof.

14. The method of claim 11, wherein the receptor tyrosine kinase inhibitor is a non-selective tyrosine kinase inhibitor.

15. The method of claim 14, wherein the non-selective tyrosine kinase inhibitor is selected from the group consisting of ponatinib, dovitinib, levatanib, ACTB-1003, Ki8751, lucitinib, masitinib, mubritinib, nintedanib, orantinib, PD089828, and a combination thereof.

16. The method of claim 1, wherein the about 100 mg of infigratinib monophosphate salt is provided as a 100 mg unit dose, by weight in its free base form.

17. The method of claim 1, wherein the about 50 mg of infigratinib monophosphate salt is provided as two 25 mg unit doses, each by weight in its free base form.

* * * * *